US012761230B2

(12) United States Patent
Wang et al.

(10) Patent No.: US 12,761,230 B2
(45) Date of Patent: Oct. 13, 2026

(54) METHOD FOR DIAGNOSING DISEASES

(71) Applicant: Newomics Inc., Berkeley, CA (US)

(72) Inventors: Daojing Wang, Moraga, CA (US); Pan Mao, Milpitas, CA (US); Weimin Ni, Palo Alto, CA (US)

(73) Assignee: Newomics Inc., Berkeley, CA (US)

( * ) Notice: Subject to any disclaimer, the term of this patent is extended or adjusted under 35 U.S.C. 154(b) by 575 days.

(21) Appl. No.: 18/220,789

(22) Filed: Jul. 11, 2023

(65) Prior Publication Data

US 2024/0133899 A1 Apr. 25, 2024
US 2024/0230679 A9 Jul. 11, 2024

Related U.S. Application Data

(63) Continuation of application No. PCT/US2021/059247, filed on Nov. 12, 2021.

(60) Provisional application No. 63/224,800, filed on Jul. 22, 2021, provisional application No. 63/138,250, filed on Jan. 15, 2021.

(51) Int. Cl.
*G01N 33/68* (2006.01)

(52) U.S. Cl.
CPC ..... *G01N 33/6896* (2013.01); *G01N 33/6848* (2013.01); *G01N 2333/4709* (2013.01); *G01N 2800/2821* (2013.01)

(58) Field of Classification Search
CPC ........... G01N 33/6896; G01N 33/6848; G01N 2333/4709; G01N 2800/2821; G01N 30/6095; G01N 2030/8831
USPC ........................................................... 436/86
See application file for complete search history.

(56) References Cited

U.S. PATENT DOCUMENTS

| | | | |
|---|---|---|---|
| 7,906,758 | B2 | 3/2011 | Stults et al. |
| 8,022,361 | B2 | 9/2011 | Wang et al. |
| 9,518,963 | B2 | 12/2016 | Prentice |
| 9,793,477 | B2 | 10/2017 | Wang et al. |
| 10,338,079 | B2 | 7/2019 | Wang et al. |
| 10,627,395 | B2 | 4/2020 | Wang et al. |
| 10,928,401 | B2 | 2/2021 | Wang et al. |
| 2003/0027347 | A1 | 2/2003 | Shapiro |
| 2004/0113068 | A1 | 6/2004 | Bousse et al. |
| 2011/0250618 | A1 | 10/2011 | Nelson et al. |
| 2011/0256580 | A1 | 10/2011 | Kim et al. |
| 2014/0110661 | A1 | 4/2014 | Wang et al. |
| 2014/0322723 | A1 | 10/2014 | Halperin et al. |
| 2015/0293063 | A1 | 10/2015 | Wang et al. |

FOREIGN PATENT DOCUMENTS

| | | | |
|---|---|---|---|
| WO | WO-2014093080 A1 | 6/2014 | |
| WO | WO-2015112429 A1 | 7/2015 | |
| WO | WO-2016183521 A1 | 11/2016 | |
| WO | WO-2022154853 A1 | 7/2022 | |

OTHER PUBLICATIONS

Klafki, Int. J. Mol. Sci. 2020, 21, 6564; doi:10.3390/ijms21186564. (Year: 2020).*

Barthelemy et al., Blood plasma phosphorylated-tau isoforms track CNS change in Alzheimer's disease, J Exp Med vol. 217 No. 11: e20200861; Jul. 28, 2020.

Bian et al., Robust, reproducible and quantitative analysis of thousands of proteomes by micro-flow LC-MS/MS, Nature Communications vol. 11, Article No. 157, Published: Jan. 9, 2020.

Bittremieux et al., Quality control in mass spectrometry-based proteomics, Mass Spectrom Rev, Sep. 2018; vol. 37, No. 5, pp. 697-711; Epub Sep. 7, 2017.

Brier et al., Tau and AB imaging, CSF measures, and cognition in Alzheimer's disease, Science Translation Medicine, vol. 8, No. 338; May 11, 2016.

Brown et al., Top-down proteomics: challenges, innovations, and applications in basic and clinical research, Expert Rev Proteomics. Oct. 2020 ; 17(10): 719-733.

Chen, et al. Qualitative and quantitative analysis of tumor cell metabolism via stable isotope labeling assisted microfluidic chip electrospray ionization mass spectrometry. Anal Chem. Feb. 7, 2012;84(3):1695-701. doi: 10.1021/ac300003k. Epub Jan. 24, 2012.

Chen, et al. Quantitation of intact proteins in human plasma using top-down parallel reaction monitoring-MS. Analytical Chemistry. vol. 90 (2018): 10650-10653.

Co-pending U.S. Appl. No. 17/167,440, inventors Wang; Daojing et al., filed Feb. 4, 2021.

Co-pending U.S. Appl. No. 17/497,172, inventors Wang; Daojing et al., filed Oct. 8, 2021.

Donnelly et al., Best practices and benchmarks for intact protein analysis for top-down mass spectrometry, Nature Methods, vol. 16, pp. 587-594; Published: Jun. 27, 2019.

Fortier, et al. Integrated microfluidic device for mass spectrometry-based proteomics and its application to biomarker discovery programs. Anal Chem. Mar. 15, 2005;77(6):1631-40.

Gallien et al., Targeted proteomic quantification on quadrupole-orbitrap mass spectrometer, Mol Cell Proteomics. Vol. 11 No. 12, pp. 1709-1723, published online Sep. 7, 2012.

Gao, et al. Characterization of drug permeability in Caco-2 monolayers by mass spectrometry on a membrane-based microfluidic device. Lab Chip. Mar. 7, 2013;13(5):978-85. doi: 10.1039/c2lc41215b. Epub Jan. 23, 2013.

Gasilova, et al. Microchip emitter for solid-phase extraction-gradient elution-mass spectrometry. Anal Chem. Jul. 2, 2013;85(13):6254-63. doi: 10.1021/ac400171e. Epub Jun. 18, 2013.

(Continued)

*Primary Examiner* — Christine T Mui
(74) *Attorney, Agent, or Firm* — WILSON SONSINI GOODRICH & ROSATI

(57) ABSTRACT

The present disclosure provides methods and systems for diagnosing diseases and monitoring their progression and therapeutic responses by detecting a presence or absence, or an increase or decrease, of one or more substances in a sample. The methods may involve microflow liquid chromatography (LC) coupled with mass spectrometry (MS) to rapidly quantitate biomarkers in a sample and identify the likelihood of the sample being positive for a disease or condition.

20 Claims, 7 Drawing Sheets

(56) References Cited

OTHER PUBLICATIONS

Han, et al. Binding of perfluorooctanoic acid to rat and human plasma proteins. Chem Res Toxicol. Jun. 2003;16(6):775-81.
Holtzman et al., Alzheimer's disease: the challenge of the second century, Sci Transl Med. vol. 3 No. 77, Apr. 6, 2011.
Iaccarino et al., Local and distant relationships between amyloid, tau and neurodegeneration in Alzheimer's Disease, Neuroimage Clin, vol. 17; pp. 452-464; Sep. 25, 2017.
International search report and written opinon dated Apr. 24, 2015 for PCT/US2015/011643.
International Search Report dated Aug. 19, 2016 for International Application No. PCT/US2016/032544.
Jack Jr et al., A/T/N: An unbiased descriptive classification scheme for Alzheimer disease biomarkers. Neurology 87(5):539-47 (2016).
Jack jr. et al., NIA-AA Research Framework: Toward a biological definition of Alzheimer's disease, Alzheimers Dement. Vol. 14 No. 4, pp. 535-562, Apr. 2018.
Jung, et al. Microchip Electrospray: Improvements in Spray and Signal Stability during Gradient Elution by an Inverted Postcolumn Makeup Flow. Analytical Chemistry, vol. 83,23: 9167-9173 (2011).
Kim, et al. Microfabricated monolithic multinozzle emitters for nanoelectrospray mass spectrometry. Anal Chem. May 15, 2007;79(10):3703-7. Epub Apr. 20, 2007.
Klafki et al., Development and Technical Validation of an Immunoassay for the Detection of APP669-711 (Aβ-3-40) in Biological Samples, International Journal of Molecular Sciences vol. 21 No. 18, Published Sep. 8, 2020.
Kuklenyik, et al. Automated solid-phase extraction and measurement of perfluorinated organic acids and amides in human serum and milk. Environ Sci Technol. Jul. 1, 2004;38(13):3698-704.
Kuklenyik, et al. Measurement of 18 perfluorinated organic acids and amides in human serum using on-line solid-phase extraction. Anal Chem. Sep. 15, 2005;77(18):6085-91.
Lau, et al. Perfluoroalkyl acids: a review of monitoring and toxicological findings. Toxicol Sci. Oct. 2007;99(2):366-94. Epub May 22, 2007.
Lee, et al. Microfluidic mixing: a review. Int J Mol Sci. 2011;12(5):3263-87. doi: 10.3390/ijms12053263. Epub May 18, 2011.
Li, et al. Profiling Cys34 adducts of human serum albumin by fixed-step selected reaction monitoring. Mol Cell Proteomics. Mar. 2011;10(3):M110.004606. doi: 10.1074/mcp.M110.004606. Epub Dec. 30, 2010.
Malinsky, et al. Determination of perfluorinated compounds in fish fillet homogenates: method validation and application to fillet homogenates from the Mississippi River. Anal Chim Acta. Jan. 10, 2011;683(2):248-57. doi: 10.1016/j.aca.2010.10.028. Epub Nov. 3, 2010.
Mao, et al., Biomonitoring of Perfluorinated Compounds in a Drop of Blood. Environ. Sci. Technol., 2015, 49 (11), pp. 6808-6814.
Mao, et al. Multinozzle emitter array chips for small-volume proteomics. Anal Chem. Jan. 15, 2013;85(2):816-9. doi: 10.1021/ac3032965. Epub Dec. 21, 2012.
Mao, et al. Multinozzle emitter arrays for nanoelectrospray mass spectrometry. Anal Chem. Aug. 1, 2011;83(15):6082-9. doi: 10.1021/ac2011813. Epub Jul. 5, 2011.
Mao, et al. Strategy for signaling molecule detection by using an integrated microfluidic device coupled with mass spectrometry to study cell-to-cell communication. Anal Chem. Jan. 15, 2013;85(2):868-76. doi: 10.1021/ac303164b. Epub Dec. 31, 2012.
Mao, et al. Top-down proteomics of a drop of blood for diabetes monitoring. J Proteome Res. Mar. 7, 2014;13(3):1560-9. doi: 10.1021/pr401074t. Epub Feb. 17, 2014.
Nakamura, Akinori et al. High Performance Plasma Amyloid-Beta Biomarkers for Alzheimer's Disease. Nature vol. 554,7691: pp. 249-254 (2018).
Nakamura, et al. The endogenous exposome. DNA Repair (Amst). Jul. 2014;19:3-13. doi: 10.1016/j.dnarep.2014.03.031. Epub Apr. 24, 2014.
Ni et al., Multiplex Mass Spectrometry Analysis of Amyloid Proteins in Human Plasma for Alzheimer's Disease Diagnosis, J Proteome Res. Aug. 6, 2021; 20(8): 4106-4112.
Olsson et al., Simultaneous measurement of β-amyloid(1-42), total tau, and phosphorylated tau (Thr181) in cerebrospinal fluid by the xMAP technology, Clinical Chemistry, vol. 51 No. 2, pp. 336-345, Feb. 2005.
Ouyang, et al. Nondestructive sampling of living systems using in vivo solid-phase microextraction. Chem Rev. Apr. 13, 2011;111(4):2784-814. doi: 10.1021/cr100203t. Epub Jan. 27, 2011.
Ovod et al., Amyloid β concentrations and stable isotope labeling kinetics of human plasma specific to central nervous system amyloidosis, Alzheimer's & Dementia vol. 13; pp. 841-849; Published online Jul. 19, 2017.
Palmqvist et al., Discriminative Accuracy of Plasma Phospho-tau217 for Alzheimer Disease vs Other Neurodegenerative Disorders, JAMA. 2020; vol. 324 No. 8, pp. 772-781; Published online Jul. 28, 2020.
PCT/US2021/059247 International Search Report and Written Opinion dated Mar. 8, 2022.
Phinney, et al. AN, et al. Development of a Standard Reference Material for metabolomics research. Anal Chem. Dec. 17, 2013;85(24):11732-8. doi: 10.1021/ac402689t. Epub Dec. 3, 2013.
Rappaport, et al. Adductomics: characterizing exposures to reactive electrophiles. Toxicol Lett. Aug. 13, 2012;213(1):83-90. doi: 10.1016/j.toxlet.2011.04.002. Epub Apr. 8, 2011.
Rappaport, et al. The blood exposome and its role in discovering causes of disease. Environ Health Perspect. Aug. 2014;122(8):769-74. doi: 10.1289/ehp.1308015. Epub Mar. 21, 2014.
Ray et al., Classification and prediction of clinical Alzheimer's diagnosis based on plasma signaling proteins, Nat Med. Nov. 2007, vol. 13 No. 11, pp. 1359-1362. Epub: Oct. 14, 2007.
Reiner, et al. Determination of perfluorinated compounds in human plasma and serum Standard Reference Materials using independent analytical methods. Anal Bioanal Chem. Nov. 2011;401(9):2899-907. doi: 10.1007/s00216-011-5380-x. Epub Sep. 9, 2011.
Renner. Growing concern over perfluorinated chemicals. Environ Sci Technol. Apr. 1, 2001;35(7):154A-160A.
Schindler et al., High-precision plasma β-amyloid 42/40 predicts current and future brain amyloidosis, Neurology, vol. 93, No. 17; Oct. 22, 2019, First published Aug. 1, 2019.
Scholl et al. , PET Imaging of Tau Deposition in the Aging Human Brain, Neuron vol. 89 No. 5, pp. 971-982; Mar. 2, 2016.
Thijssen et al., Diagnostic value of plasma phosphorylated tau181 in Alzheimer's disease and frontotemporal lobar degeneration, Nat Med. Mar. 2020, vol. 26, No. 3, pp. 387-397, Epub Mar. 2, 2020.
U.S. Appl. No. 16/412,039 Notice of Allowance dated Oct. 14, 2020.
U.S. Appl. No. 15/203,666 Notice of Allowance dated Apr. 19, 2019.
U.S. Appl. No. 15/203,666 Office Action dated Feb. 8, 2019.
U.S. Appl. No. 15/203,666 Office Action dated Sep. 18, 2018.
U.S. Appl. No. 15/786,949 Notice of Allowance dated Feb. 20, 2020.
U.S. Appl. No. 15/786,949 Office Action dated Oct. 8, 2019.
U.S. Appl. No. 16/412,039 Office Action dated Mar. 13, 2020.
Villeneuve et al., Existing Pittsburgh Compound-B positron emission tomography thresholds are too high: statistical and pathological evaluation, Brain, vol. 138, pp. 2022-2033; Advance Access publication date: May 7, 2015.
Vuckovic, et al. Solid-phase microextraction in bioanalysis: New devices and directions. J Chromatogr A. Jun. 18, 2010;1217(25):4041-60. doi: 10.1016/j.chroma.2009.11.061. Epub Dec. 4, 2009.
Wang, et al. Single cell analysis: the new frontier in 'omics'. Trends Biotechnol. Jun. 2010;28(6):281-90. doi: 10.1016/j.tibtech.2010.03.002. Epub Apr. 29, 2010.
Yaffe et al., Association of plasma beta-amyloid level and cognitive reserve with subsequent cognitive decline, JAMA vol. 305, No. 3, pp. 261-266; Jan. 19, 2011.
Yang, et al. Coupling on-chip solid-phase extraction to electrospray mass spectrometry through an integrated electrospray tip. Electrophoresis. Oct. 2005;26(19):3622-30.

(56) References Cited

OTHER PUBLICATIONS

Ying, et al. Microfluidic chip-based technologies: emerging platforms for cancer diagnosis. BMC Biotechnol. Sep. 27, 2013;13:76. doi: 10.1186/1472-6750-13-76.
Yu, et al. Monolithic porous polymer for on-chip solid-phase extraction and preconcentration prepared by photoinitiated in situ polymerization within a microfluidic device. Anal Chem. Nov. 1, 2001;73(21):5088-96.

* cited by examiner

METHOD FOR DIAGNOSING DISEASES

CROSS-REFERENCE

This application is a continuation of International Application No. PCT/US2021/059247, filed Nov. 12, 2021, which claims the benefit of U.S. Provisional Patent Application No. 63/224,800, filed on Jul. 22, 2021, and U.S. Provisional Patent Application No. 63/138,250, filed on Jan. 15, 2021, each of which applications is incorporated herein by reference in its entirety.

STATEMENT AS TO FEDERALLY SPONSORED RESEARCH

This invention was made with government support under Contract number AG046025 awarded by National Institutes of Health. The government has certain rights in the invention.

BACKGROUND

The proteome may be reflective of the physiological and pathological states of a subject. Proteomics is a powerful tool for diagnostics of diseases and monitoring of therapeutic responses. The majority of current protein assays in clinical settings are based on enzyme-linked immunosorbent assay (ELISA) immunoassays, which may require high-quality antibodies and may be hard to achieve with high multiplexing (e.g., greater than 10) due to the cross-reactivity of antibodies. Mass spectrometry (MS) measures the mass-to-charge ratio of charged species and may be an enabling technology for proteomics. Aside from de novo identification of target proteins, MS has advantages over ELISA for detecting protein mutations, modification, truncations, and adductations, for example. Once combined with liquid chromatography (LC), liquid chromatography mass spectrometry (LC-MS) may enable separation, identification, characterization, and quantitation of complex mixtures of proteins and peptides and their isoforms. Such quantitation may be used to diagnose or monitor disease or physiological states.

SUMMARY

Recognized herein are various issues with systems currently available for disease detection, diagnosis and/or monitoring. For instance, current systems may require large sample sizes, significant processing times, or high cost, which make such systems impractical for use in various diagnostics applications, including point of care applications. Accordingly, recognized herein is a need for a platform that can achieve robustness, sensitivity, and throughput for analysis of small-volume samples (or biospecimens).

Such small-volume samples may contain small quantities of biomarkers that can be quantified by sufficiently sensitive techniques. Additionally, sensitive techniques may be able to detect biomarkers early in disease progression or before disease onset when therapeutic intervention is likely to be more effective.

One disease which may benefit from increased early and sensitive detection is Alzheimer's disease (AD). AD is a devastating neurodegenerative disease that affects more than 30 million people (including 5 million Americans) worldwide, and this number is expected to reach more than 120 million by the year 2050. Although AD is typically diagnosed postmortem, detection of the key constituents of AD pathology, the β-amyloid (Ab) plaque and pathological forms of tau are measurable with PET scans of the brain, or by immunoassays of Aβ1-42 and Ab1-40, as well as Tau/pTau (ELISA or xMAP) in CSF. On the other hand, minimally invasive (e.g., blood-based), reproducible, and cost-effective assays for specific biomarkers can facilitate early diagnosis and accelerate therapeutic development for AD. Progress has been made in recent years on detecting AD biomarkers in human blood samples. However, current assays have not yet achieved the optimum combination of sensitivity, specificity, and reproducibility for multiplex clinical diagnostics. For example, immunoassays may suffer from cross-reactivity between antibodies, matrix interference, and potential interference from endogenous antibodies in patients. Compared to the traditional immunoassays, mass spectrometry (MS)-based assays can achieve high specificity as well as high precision using stable isotope-labeled internal standards. However, the current matrix-assisted laser desorption ionization (MALDI) method lacks automation, and the bottom-up nanoflow LC-MS method requires trypsin digestion of IP products for quantitating the amyloid proteins at the peptide level, which increases labor and reduces accuracy and reproducibility.

Intact protein including top-down LC-MS analysis has progressed rapidly due to the recent advances in LC separation, high resolution mass spectrometry, and data analysis. In addition, there has been a renewed interest in microflow rather than highflow or nanoflow LC-MS for clinical analysis due to its sensitivity, robustness, and throughput. The present disclosure provides a microflow LC-targeted MS assay for detecting and/or quantifying biomolecules that are associated with certain health or physiological condition or disease (e.g., proteins including 4 intact β-amyloid proteins) from a biological sample (e.g., human plasma IP samples). Based on the presence, absence, and/or quantities of the biomolecules, whether or not a subject from which the biological sample is obtained has the health or physiological condition or disease can be determined. In some cases, the determination comprises determining a likelihood that the biological sample or the subject is positive or negative for a given health or physiological condition or disease. Compared to conventional methods such as the nanoflow LC-MS method, methods of the present disclosure are equally accurate and sensitive, with the additional benefits of higher throughput and reduced labor, as demonstrated in a prospective clinical study. Thus the methods may promote large-scale screening of the older population for early diagnosis of diseases.

An aspect of the present disclosure provides for a method for determining a likelihood that a subject has a health or physiological condition or disease, the method comprising: (a) enriching a biological sample of the subject for proteins that are associated with the condition or disease; (b) directing a liquid medium comprising at least a subset of the proteins enriched in (a) to flow through a microfluidic device to separate individual proteins of the at least the subset of the proteins from one another, the liquid medium having a volume of less than 25 microliters (μL); (c) directing the individual proteins separated in (b) to a mass spectrometer to generate signals assignable to the individual proteins or fragments thereof; and (d) determining, based at least in part on the signals, the likelihood that the subject is positive for the condition or disease.

In some embodiments, the liquid medium has a volume of less than 20 μL. In some embodiments the liquid medium has a volume of less than 10 μL. In some embodiments, the liquid medium has a volume of less than 5 μL. In some embodiments, the liquid medium has a volume of less than 3 μL. In some embodiments, the liquid medium has a volume of less than 1 μL. In some embodiments, the determining of (d) comprises determining a quantity of one or more of the individual proteins. In some embodiments, the determining of (d) comprises determining a quantity for each of the individual proteins. In some embodiments, the determining of (d) further comprises determining a ratio of at least two of the individual proteins. In some embodiments, the condition or disease is a neurodegenerative disease. In some embodiments, the neurodegenerative disease is Alzheimer's Disease. In some embodiments, the proteins comprise amyloid proteins. In some embodiments, the proteins comprise β-amyloid proteins. In some embodiments, the proteins comprise Aβ38, APP669-711, Aβ40, Aβ42, or any combination thereof. In some embodiments, the determining of (d) further comprises determining a ratio of Aβ40 and Aβ42. In some embodiments, the determining of (d) further comprises determining a ratio of APP669-711 and Aβ42. In some embodiments, the likelihood is identified at an accuracy of greater than or equal to about 80%. In some embodiments, the likelihood is identified at an accuracy of greater than or equal to about 85%. In some embodiments, the likelihood is identified at an accuracy of greater than or equal to about 90%. In some embodiments, the biological sample comprises a bodily fluid. In some embodiments, the biological sample is a blood sample. In some embodiments, the blood sample is a whole blood sample. In some embodiments, the blood sample is a plasma sample. In some embodiments, the blood sample is a serum sample. In some embodiments, the enriching comprises performing an immunoprecipitation, an enzyme-linked immunoassay (ELISA), a ligand binding assay (LBA), a radioimmunoassay (RIA), or any combination thereof. In some embodiments, the mass spectrometer is a quadrupole and/or orthogonal time of flight mass spectrometer. In some embodiments, the mass spectrometer is an orbitrap. In some embodiments, the mass spectrometer is not a matrix-assisted laser desorption ionization (MALDI) mass spectrometer.

In another aspect, the present disclose provides for a method for determining a likelihood that a subject has a health or physiological condition or disease, comprising: (a) enriching a biological sample of the subject for proteins that are associated with the condition or disease; (b) directing a liquid medium comprising at least a subset of the proteins enriched in (a) to flow through a microfluidic device at a flow rate of greater than 1 microliter/minute (μL/min) to separate individual proteins of the at least the subset of the proteins from one another; (c) directing the individual proteins separated in (b) to a mass spectrometer to generate signals assignable to the individual proteins or fragments thereof; and (d) determining, based at least in part on the signals of (c), the likelihood that the subject is positive for the condition or disease.

In some embodiments, the flow rate is greater than or equal to about 1.5 L/min. In some embodiments, the flow rate is greater than or equal to about 2.0 μL/min. In some embodiments, the flow rate is greater than or equal to about 5.0 μL/min. In some embodiments, the flow rate is greater than or equal to about 10.0 μL/min. In some embodiments, the determining of (d) comprises determining a quantity of one or more of the individual proteins. In some embodiments, the determining of (d) comprises determining a quantity for each of the individual proteins. In some embodiments, the determining of (d) further comprises determining a ratio of at least two of the individual proteins. In some embodiments, the condition or disease is a neurodegenerative disease. In some embodiments, the neurodegenerative disease is Alzheimer's Disease. In some embodiments, the proteins comprise amyloid proteins. In some embodiments, the proteins comprise β-amyloid proteins. In some embodiments, the proteins comprise Aβ38, APP669-711, Aβ40, Aβ42, or any combination thereof. In some embodiments, the determining of (d) further comprises determining a ratio of Aβ42 and Aβ40. In some embodiments, the determining of (d) further comprises determining a ratio of APP669-711 and Aβ42. In some embodiments, the likelihood is identified at an accuracy of greater than or equal to about 80%. In some embodiments, the likelihood is identified at an accuracy of greater than or equal to about 85%. In some embodiments, the likelihood is identified at an accuracy of greater than or equal to about 90%. In some embodiments, the biological sample comprises a bodily fluid. In some embodiments, the biological sample is a blood sample. In some embodiments, the blood sample is a whole blood sample. In some embodiments, the blood sample is a plasma sample. In some embodiments, the blood sample is a serum sample. In some embodiments, the enriching comprises performing an immunoprecipitation, an enzyme-linked immunoassay (ELISA), a ligand binding assay (LBA), a radioimmunoassay (RIA), or any combination thereof. In some embodiments, the mass spectrometer is a quadrupole and/or orthogonal time of flight mass spectrometer. In some embodiments, the mass spectrometer is an orbitrap. In some embodiments, the mass spectrometer is not a matrix-assisted laser desorption ionization (MALDI) mass spectrometer.

In another aspect, the present disclosure provides for a method for determining a likelihood that a subject has a health or physiological condition or disease, comprising: (a) enriching a biological sample of the individual for proteins that are associated with the condition or disease; (b) directing a liquid medium comprising at least a subset of the proteins enriched in (a) to flow through a microfluidic device to separate individual proteins of the at least the subset of the proteins from one another; (c) directing the individual proteins separated in (b) to a mass spectrometer to generate signals assignable to the individual proteins or fragments thereof, wherein the individual proteins are not subjected to an enzymatic digestion process prior to (c); and (d) determining, based at least in part on the signals of (c), the likelihood that the subject is positive for the condition or disease.

In some embodiments, the individual proteins are intact proteins. In some embodiments, the determining of (d) comprises determining a quantity of one or more of the individual proteins. In some embodiments, the determining of (d) comprises determining a quantity for each of the individual proteins. In some embodiments, the determining of (d) further comprises determining a ratio of at least two of the individual proteins. In some embodiments, the condition or disease is a neurodegenerative disease. In some embodiments, the neurodegenerative disease is Alzheimer's Disease. In some embodiments, the proteins comprise amyloid proteins. In some embodiments, the proteins comprise β-amyloid proteins. In some embodiments, the proteins comprise Aβ38, APP669-711, Aβ40, Aβ42, or any combination thereof. In some embodiments, the determining of (d) further comprises determining a ratio of Aβ42 and Aβ40. In some embodiments, the determining of (d) further comprises determining a ratio of APP669-711 and Aβ42. In some embodiments, the method further comprises determining the likelihood when the quantity of the one or more of the individual proteins is above a pre-determined threshold. In some embodiments, the pre-determined threshold is between 8 μg/mL and 600 μg/mL. In some embodiments, the method further comprises determining the likelihood when the ratio of Aβ42 and Aβ40 is below a pre-determined threshold. In some embodiments, the pre-determined threshold is between 0 and 0.1770. In some embodiments, the pre-determined threshold is about 0.1485. In some embodiments, the method further comprises determining the likelihood when the ratio of APP669-711 and Aβ42 is above a pre-determined threshold. In some embodiments, the likelihood is identified at an accuracy of greater than or equal to about 80%. In some embodiments, the likelihood is identified at an accuracy of greater than or equal to about 85%. In some embodiments, the likelihood is identified at an accuracy of greater than or equal to about 90%. In some embodiments, the biological sample comprises a bodily fluid. In some embodiments, the biological sample is a blood sample. In some embodiments, the blood sample is a whole blood sample. In some embodiments, the blood sample is a plasma sample. In some embodiments, the blood sample is a serum sample. In some embodiments, the enriching comprises performing an immunoprecipitation, an enzyme-linked immunoassay (ELISA), a ligand binding assay (LBA), a radioimmunoassay (RIA), or any combination thereof. In some embodiments, the mass spectrometer is a quadrupole and/or orthogonal time of flight mass spectrometer. In some embodiments, the mass spectrometer is an orbitrap. In some embodiments, the mass spectrometer is not a matrix-assisted laser desorption ionization (MALDI) mass spectrometer.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1B:
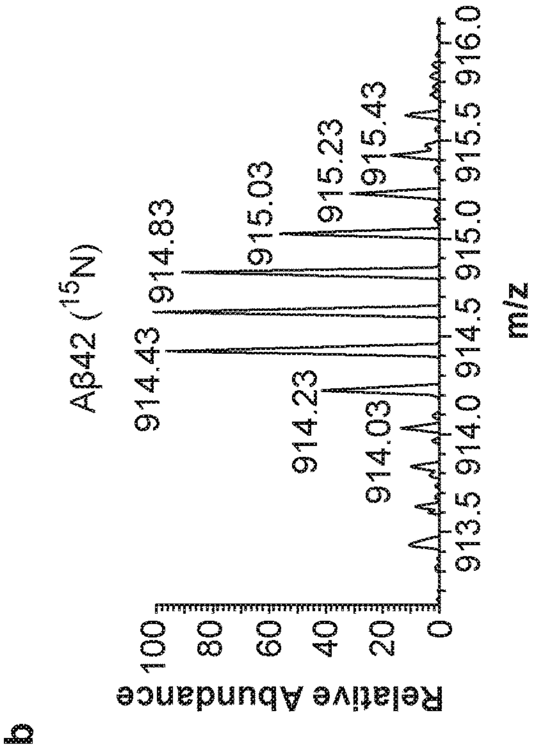
FIG. 1B depicts a targeted MS1 mass spectrum of $^{15}$N Aβ42 showing all expected isotopic peaks.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least" or "greater than" applies to each one of the numerical values in that series of numerical values.

Whenever the term "no more than," "less than," or "less than or equal to" precedes the first numerical value in a series of two or more numerical values, the term "no more than" or "less than" applies to each one of the numerical values in that series of numerical values.

The term "about" or "nearly" as used herein generally refers to within (plus or minus) 15%, 10%, 9%, 8%, 7%, 6%, 5%, 4%, 3%, 2%, or 1% of a designated value.

As used herein, the singular forms "a", "an", and "the" include plural references unless the context clearly dictates otherwise.

The term "biomarker," as used herein, generally refers to any substances (e.g., composition and/or molecules), or a complex of substances, which is associated with a biological state or condition of an organism, such as a subject. Examples of such biological state or condition include, without limitation, a disease, a disorder, a non-disease condition, or therapeutic responses to different drug treatments and other therapies.

The term "subject," as used herein generally refers to any living being comprised of at least one cell. An organism can be a single cell organism or a multi-cellular organism, such as a mammal, a non-mammal (e.g., a bird), or a plant (e.g., a tree). An organism may be a mammal, such as, for example, a human or an animal such as a primate (e.g., a monkey, chimpanzee, etc.), a domesticated animal (e.g., a dog, cat, etc.), farm animal (e.g., goat, sheep, pig, cattle, horse, etc.), or laboratory animal (e.g., mouse, rat, etc.). A subject may be a patient. A subject may be an individual that has or is suspected of having a disease.

Examples of subjects may include, but not limited to, humans, mammals, non-human mammals, rodents, amphibians, reptiles, canines, felines, bovines, equines, goats, ovines, hens, avines, mice, rabbits, insects, slugs, microbes, bacteria, parasites, or fish. In some cases, the subject may be a patient who is having, suspected of having, or at a risk of developing a disease or disorder. In some cases, the subject may be a pregnant woman. The subject may be a normal healthy pregnant woman, or a pregnant woman who is at risk of carrying a baby with certain birth defect.

Overview

The present disclosure provides methods and systems for sample processing and data analysis. In some cases, sample processing includes assaying or having assayed (e.g., purifying and/or isolating) proteins or other biological molecules of interest from a sample. The sample or a portion, fraction, component, or isolate thereof may be subject to further analysis. The analysis may comprise separating one or more biomolecules (e.g., proteins) from a (processed) sample and detecting the presence or absence of certain biomolecules. Based on the detected presence or absence of the certain biomolecules, the sample may be determined as positive or likely of having a disease or physiological condition or at risk of developing the disease or condition.

The methods described herein may comprise enriching a biological sample for biomolecules (e.g., biomarkers, e.g., proteins) associated with a condition or disease. At least a subset of the enriched biomolecules or a volume containing them may then be directed through a microfluidic device to separate individual proteins of the subset of enriched proteins. The volume containing the enriched proteins may be relatively small (e.g., less than 25 μL in volume). The individual separated proteins or fragments thereof may then be directed through a detector, such as a mass spectrometer, which generates signals assignable to the individual proteins or fragments thereof. Based on the signals, the identities of the individual proteins and/or their quantities in the sample may be determined. From such information, the likelihood that the biological sample is positive for the condition or disease may then be determined.

In some cases, the methods described herein may comprise enriching a biological sample for biomolecules (e.g., biomarkers such as proteins) associated with a condition or disease. At least a subset of the enriched biomolecules or a volume containing them may then be directed through a microfluidic device to separate individual proteins of the subset of enriched proteins. The volume containing the enriched proteins may be directed to flow through the microfluidic device at a particular flow rate (e.g., greater than 1 microliter/minute [μL/min]). The individual separated proteins or fragments thereof may then be directed through a detector, such as a mass spectrometer, which generates signals assignable to the individual proteins or fragments thereof. Based on the signals, the identities of the individual proteins and/or their quantities in the sample may be determined. From such information, the likelihood that the biological sample is positive for the condition or disease may then be determined.

In some cases, the methods described herein may comprise enriching a biological sample for biomolecules (e.g., biomarkers, e.g., proteins) associated with a condition or disease. At least a subset of the enriched biomolecules or a volume containing them may then be directed through a microfluidic device to separate individual proteins of the enriched proteins. The individual separated proteins may then be directed through a detector, such as a mass spectrometer, which generates signals assignable to the individual proteins or fragments thereof. The individual proteins may not be subjected to an enzymatic digestion process prior to being directed through the mass spectrometer. Based on the signals, the identities of the individual proteins and/or their quantities in the sample may be determined. From such information, the likelihood that the biological sample is positive for the condition or disease may then be determined.

Biological Samples

Methods and systems provided herein may be used for diagnosing, detecting or identifying a disease or health or physiological condition of a subject by analyzing a biological sample. The method may involve analyzing a biological sample or part thereof to determine a likelihood the sample is positive for a disease or health condition. Alternatively or additionally, the method may include diagnosing a subject with the disease or health condition, monitoring the disease or health condition in the subject, and/or determining a propensity of the subject for the health disease/condition.

Any substance that is measurable may be the source of a sample. The substance may be a fluid, e.g., a biological fluid. A fluidic substance may include, but is not limited to, blood (e.g., whole blood, plasma, serum), cord blood, saliva, urine, sweat, serum, semen, vaginal fluid, gastric and digestive fluid, cerebrospinal fluid, placental fluid, cavity fluid, ocular fluid, serum, breast milk, lymphatic fluid, or combinations thereof.

The substance may be solid, for example, a biological tissue. The substance may comprise normal healthy tissues. The tissues may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

The substance may comprise tumors. Tumors may be benign (non-cancer) or malignant (cancer). Non-limiting examples of tumors may include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof. The tumors may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

The substances may comprise a mix of normal healthy tissues or tumor tissues. The tissues may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

In some cases, the substance may comprise a variety of cells, including, but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, and circulating cells in the human blood. In some cases, the substance may comprise contents of a cell, such as, for example, the contents of a single cell or the contents of multiple cells.

In some cases, the substances may comprise one or more markers whose presence or absence is indicative of some phenomenon such as disease, disorder, infection, or environmental exposure. A marker can be, for example, a cell, a small molecule, a macromolecule, a protein, a glycoprotein, a carbohydrate, a sugar, a polypeptide, a nucleic acid (e.g., deoxyribonucleic acid (DNA), ribonucleic acid (RNA)), a cell-free nucleic acid (e.g., cf-DNA, cf-RNA), a lipid, a cellular component, or combinations thereof.

In some cases, a marker can be a biomarker. Non-limiting examples of biomarkers may include glycated proteins, glycated hemoglobin (HbA1c), HbA-Glyc, HbA-SNO, glycated albumin (GA), glucose (e.g., fasting plasma glucose), human serum albumin (HSA), HSA-Cys, HSA-Glyc, apolipoprotein A-I (apoA-I), apoA-I MetO, GA, glycated apolipoprotein A-1 (GapoA-I), Alpha-fetoprotein (AFP), philadelphia chromosome (BCR-ABL), breast cancer type 1 susceptibility protein (BRCA1), breast cancer type 2 susceptibility protein (BRCA2), v-Raf murine sarcoma viral oncogene homolog B (BRAF V600E), carcinoma antigen 125 (CA-125), carbohydrate antigen 19-9 (CA19.9), Zn-α2 glycoprotein (ZAG), carcinoembryonic antigen (CEA), epidermal growth factor receptor (EGFR), receptor tyrosine-protein kinase erbB-2 (HER-2), mast/stem cell growth factor receptor (KIT), prostate-specific antigen (PSA), S-100 proteins (S100), total tau (T-tau), hyperphosphorylated tau (P-tau), 42 amino acid isoform of amyloid β (Aβ42), cytokines (e.g., interleukin (IL)-1, IL-6, IL-8, Il-10, IL-1β, IL-1Ra, TNF-α monocyte chemoattractant protein-1 (MCP-1) etc.), soluble CD40 ligand, serum amyloid A (SAA), selectins (e.g., E-selectin, P-selectin), myeloperoxidase (MPO), matrix metalloproteinases (MMPs), cellular adhesion molecules (e.g., intercellular adhesion molecule 1 (ICAM-1), vascular adhesion molecule 1 (VCAM-1)), placental growth factor (PIGF), $A_2$ phospholipases, high-sensitivity C-reactive protein (hs-CRP), metalloproteinases (MMP-9, MMP-11), pregnancy-associated plasma protein A (PAPP-A), cathepsin S, chemotactic molecules (MCP-1, CCR1, CCR2), myeloperoxidase, neopterin, growth differentiation factor-15, placental growth factor, markers of fibrosis (e.g., galectin-3), fetuin-A, vascular calcification (osteoprogenterin), myeloid-related proteins 8/14 (MRP8/14), pentraxin 3 (PTX3), osteoprotegerin, von Willebrand factor (vWF), tissue factor (TF), soluble CD40 ligand (sCD40L), prothrombin fragment 1.2 (F1.2), thrombus precursor protein (TpP), D dimer, Lp-PLA2 mass, oxidized amino acids, oxidised apolipoprotein A1 (apoA1), asymmetric dimethylarginine (ADMA), secretory phospholipase, high-sensitivity cardiac troponin, malondialdehyde-modified low-density lipoprotein, heart-type Fatty Acid-Binding Protein (H-FABP), B-type natriuretic peptide (BNP), N-terminal pro b-type natriuretic peptide (NT-proBNP), copeptin, mid-region pro-adrenomedullin, urocortin-1, arginine vasopressin (AVP), endothelin-1, galectin-3, ST-2, cystatin-C, neutrophil gelatinase-associated lipocalin (NGAL), KIM, adiponectin, leptin, resistin, c-peptide, phospholipid fatty acids (EPA and DHA), apolipoprotein E (ApoE), Cholesteryl ester transfer protein (CETP), S100 calcium binding protein B (S100 Beta), Neuron-specific enolase (NSE), and fractions, derivatives or combinations thereof.

Samples may be obtained from various subjects at various time intervals. In some examples, samples are obtained from a subject at least every 30 seconds, 1 minute, 10 minutes, 30 minutes, 1 hour, 2 hours, 3 hours, 4 hours, 5 hours, 6 hours, 12 hours, 1 day, 1 month, or longer.

A sample may be obtained from a subject using various approaches. For example, a sample may be obtained from a subject through accessing the circulatory system (e.g., intravenously or intra-arterially via a syringe, fingerstick, fingerprick, or other apparatus), collecting a secreted biological sample (e.g., saliva, sputum urine, feces, etc.), surgically (e.g., biopsy) acquiring a biological sample (e.g., intra-operative samples, post-surgical samples, etc.), swabbing (e.g., buccal swab, oropharyngeal swab), or pipetting. Such approaches may be used to obtain a biological sample of substantially low volume (e.g., less than or equal to about 5 microliters) form the subject.

A sample can be transported to a facility for analysis. The facility may be onsite or a local facility, e.g., a facility within a clinic or hospital where the sample is collected. The facility may also be an offsite or remote facility which may necessitate shipment of samples.

Samples may be stored and transported in a container. The container may be the same as the sample collection container. The container may be a transport container. The transport container may contain the sample collection container. The transport container may comprise one or more of indentations configured to accommodate one or more of sample containers. The transport container may be in communication with the sample collection container. The transport container may be empty. The transport container may comprise a secondary container. The transport container may be insulated. The secondary container may be insulated. The secondary container may be hermetically sealed. The transport container may comprise a plurality of cooling packets containing a cryogenic material (e.g., cooling packs or dry ice). The transport container may comprise a desiccant. Non-limiting examples of desiccants may include silica, activated charcoal, calcium sulfate, calcium chloride, molecular sieves, or combinations thereof. The desiccant may have a dye indicator. The dye indicator can be reactive with moisture. The transport container may comprise a temperature control module to maintain a pre-set shipping temperature. The transport container can be accommodated in an incubator. The transport container can be heated in an incubator. The transport container may be part of, or integrate with, a system for keeping cells alive. The transport container can comprise a data-logging device. The data-logging device can be programmable. The data-logging device may be configured to monitor and record the change of one or more of parameters concerning the sample during transportation. Non-limiting examples of parameters may include temperature, moisture, pressure, gas level, or a combination thereof. The data-logging device may generate a report regarding the status of the sample being shipped. The data-logging device may directly contact the transport container. The data-logging device may be attached to the transport container. The data-logging device may be separable with the transport container.

The shipping or handling time for each sample may vary depending upon, e.g., the method by which the sample is collected or prepared. The total shipping and handling time as measured from sample collection until sample processing may be less than 1 hour, less than 2 hours, less than 3 hours, less than 4 hours, less than 5 hours, less than 6 hours, less than 7 hours, less than 8 hours, less than 9 hours, less than 10 hours, less than 11 hours, less than 12 hours, less than 13 hours, less than 14 hours, less than 15 hours, less than 16 hours, less than 17 hours, less than 18 hours, less than 19 hours, less than 20 hours, less than 21 hours, less than 22 hours, less than 23 hours, or less than 24 hours. In some cases, a shipped sample may be time-stamped to provide a measure of shipping and handling times.

A sample may or may not be processed before being delivered into a microfluidic device or other device for detection and analysis. In cases where a sample processing is needed, various types of processing methods or techniques may be employed. By way of non-limiting example, a processing method may include, for example, (i) diluting an aliquot of each sample with a certain amount of buffer (e.g., phosphate buffered saline (PBS)) and centrifuging the mixture (or diluted sample) under certain conditions (e.g., at a speed of 3,000 g for 5 min at room temperature (RT)); (ii) reconstituting an aliquot (e.g., 5 μL) of the supernatant in a solvent, and subsequently centrifuging the mixture under certain conditions (e.g., at 14,000 g for 5 min at RT) to remove any cellular debris; (iii) collecting the supernatant obtained from step (ii) and storing it as the plasma portion; (iv) washing the cell pellet derived from the first centrifuge step with a buffer (e.g., PBS buffer) at least one time and incubating the washed pellet under certain conditions (e.g., for 2 hours at 37° C.); (v) lysing the cells by, e.g., suspending the cell pellet in certain amount of HPLC-grade water and vortexing for a period of time at RT, constituting the hemolysate in the solvent and centrifuging, e.g., at 14,000 g for 5 min. A certain amount of supernatant may then be collected and stored as the hemolysate portion. Finally, an artificial mixture of a solution may be generated by mixing at least a part of the plasma portion, the hemolysate portion and the solvent. An aliquot of the artificial mixture may then be injected onto the microfluidic device for analysis.

A quantity of total input sample that can be used in the methods provided herein may vary. In some cases, a high quantity of input sample may be used. In some cases, a low quantity of input sample may be used. In some cases, the quantity of input samples may be greater than or equal to about 1 picogram (pg), 10 pg, 25 pg, 50 pg, 100 pg, 250 pg, 500 pg, 750 pg, 1 nanogram (ng), 5 ng, 10 ng, 25 ng, 50 ng, 75 ng, 80 ng, 90 ng, 100 ng, 200 ng, 300 ng, 400 ng, 500 ng, 600 ng, 700 ng, 800 ng, 900 ng, 1 microgram (μg), 2 μg, 3 μg, 4 μg, 5 μg, 6 μg, 7 μg, 8 μg, 9 μg, 10 μg, 12 μg, 14 μg, 16 μg, 18 μg, 20 μg, 25 μg, 30 μg, 35 μg, 40 μg, 50 μg, 40 μg, 70 μg, 80 μg, 90 μg, 100 μg, 200 μg, 300 μg, 400 μg, 500 μg, 750 μg, 1 milligram (mg), 5 mg, 10 mg, 25 mg, 50 mg, 75 mg, 100 mg or more. In some cases, the quantity of input samples may be less than or equal to about 1 gram (g), 500 mg, 250 mg, 100 mg, 50 mg, 25 mg, 10 mg, 5 mg, 1 mg, 750 μg, 500 μg, 250 μg, 125 μg, 100 μg, 75 μg, 50 μg, 40 μg, 30 μg, 25 μg, 20 μg, 19 μg, 18 μg, 17 μg, 16 μg, 15 μg, 14 μg, 13 μg, 12 μg, 11 μg, 10 μg, 9 μg, 8 μg, 7 μg, 6 μg, 5 μg, 4 μg, 3 μg, 2 μg, 1 μg, 900 ng, 800 ng, 700 ng, 600 ng, 500 ng, 400 ng, 300 ng, 200 ng, 100 ng, 75 ng, 50 ng, 25 ng, 10 ng, 5 ng, 1 ng, 750 pg, 500 pg, 250 pg, 100 pg, 50 pg, 25 pg, 10 pg, 1 pg or less. In some cases, the quantity of input sample may fall into a range between any two of the values described herein.

In some examples, input sample may comprise one or more substances that are to be detected or identified. The substances of interest or the target substances (e.g., substances associated with a disease or disorder) may make up a certain percentage of the total sample input. For example, a sample may comprise a plurality of proteins and only a few of the proteins (e.g., 5% or less, 1% or less) that are associated with or indicative of certain type of diseases or conditions are the substances of interest. In some cases, the target substances may make up a high percentage of the total input. In some cases, the target substances may make up a low percentage of the total input. In some cases, the target substances may make up less than or equal to about 100%, 95%, 90%, 80%, 70%, 60%, 50%, 40%, 30%, 20%, 10%, 5%, 1%, 0.75%, 0.5%, 0.25%, 0.1%, 0.075%, 0.05%, 0.025%, 0.01%, 0.0075%, 0.005%, 0.0025%, 0.001%, 0.00075%, 0.005%, 0.0025%, 0.001%, 0.00075%, 0.0005%, 0.00025%, 0.0001%, 0.000075%, 0.00005%, 0.000025%, 0.00001% or less of the total input. In some cases, the target substances may make up at least about 0.000001%, 0.000005%, 0.0000075%, 0.00001%, 0.00005%, 0.000075%, 0.0001%, 0.0005%, 0.00075%, 0.001%, 0.005%, 0.0075%, 0.01%, 0.05%, 0.075%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, 99%, 99.99% or more of the total input. In some cases, the percentage of the target substances may be between any of the two values described herein.

The quantity of input target substances may vary. In some cases, a high quantity of target substances may be included. In some cases, a low quantity of target substances may be included. In some cases, at least about 1 femtogram (fg), 5 fg, 10 fg, 25 fg, 50 fg, 100 fg, 200 fg, 300 fg, 400 fg, 500 fg, 600 fg, 700 fg, 800 fg, 900 fg, 1 pg, 5 pg, 10 pg, 25 pg, 50 pg, 100 pg, 200 pg, 300 pg, 400 pg, 500 pg, 600 pg, 700 pg, 800 pg, 900 pg, 1 ng, 2.5 ng, 5 ng, 10 ng, 25 ng, 50 ng, 75 ng, 100 ng, 200 ng, 300 ng, 400 ng, 500 ng, 600 ng, 700 ng, 800 ng, 900 ng, 1 μg, 2 μg, 3 μg, 4 μg, 5 μg, 6 μg, 7 μg, 8 μg, 9 μg, 10 μg, 15 μg, 20 μg, 30 μg, 40 μg, 50 μg, 75 μg, 100 μg, 250 μg, 500 μg, 750 μg, 1 mg, 10 mg, 25 mg, 50 mg, 100 mg or more of target substances may be inputted. In some cases, less than or equal to about 1 g, 500 mg, 250 mg, 100 mg, 50 mg, 25 mg, 10 mg, 5 mg, 1 mg, 750 μg, 500 μg, 250 μg, 100 μg, 80 μg, 60 μg, 50 μg, 40 μg, 30 μg, 20 μg, 18 μg, 16 μg, 14 μg, 12 μg, 10 μg, 9 μg, 8 μg, 7 μg, 6 μg, 5 μg, 4 μg, 3 μg, 2 μg, 1 μg, 900 ng, 800 ng, 700 ng, 600 ng, 500 ng, 400 ng, 300 ng, 200 ng, 100 ng, 75 ng, 50 ng, 25 ng, 10 ng, 5 ng, 1 ng, 500 pg, 250 pg, 100 pg, 50 pg, 25 pg, 10 pg, 5 pg, 1 pg or less of target substances may be inputted. In some cases, the quantity of inputted target substances may fall into a range between any of the two values described herein.

A volume of the sample that can be used in the methods provided herein may vary. As provided herein, methods and systems can be adapted or configured to perform functions on a sample having either a large or a small volume. As will be appreciated, in some cases, it may be preferred to have methods or systems that can support highly-sensitive analysis on very little sample.

For example, in some cases, less than or equal to about 1000 μL, 900 μL, 800 μL, 700 μL, 600 μL, 500 μL, 400 μL, 300 μL, 200 μL, 100 μL, 90 μL, 80 μL, 70 μL, 60 μL, 50 μL, 45 μL, 40 μL, 35 μL, 30 μL, 25 μL, 20 μL, 15 μL, 10 μL, 9 μL, 8 μL, 7 μL, 6 μL, 5 μL, 4 μL, 3 μL, 2 μL, 1 μL, 900 nL, 800 nL, 700 nL, 600 nL, 500 nL, 400 nL, 300 nL, 200 nL, 100 nL, 75 nL, 50 nL, 25 nL, 10 nL, 1 nL, 750 picoliter (pL), 500 pL, 250 pL, 100 pL, 75 pL, 50 pL, 25 pL, 10 pL, 5 pL, 1 pL or less of the sample may be used. In some cases, more than or equal to about 1 pL, 5 pL, 10 pL, 25 pL, 50 pL, 75 pL, 100 pL, 250 pL, 500 pL, 750 pL, 1 nL, 10 nL, 25 nL, 50 nL, 75 nL, 100 nL, 200 nL, 300 nL, 400 nL, 500 nL, 600 nL, 700 nL, 800 nL, 900 nL, 1 μL, 2 μL, 3 μL, 4 μL, 5 L, 6 μL, 7 μL, 8 μL, 9 μL, 10 μL, 11 μL, 12 μL, 13 μL, 14 μL, 15 μL, 16 μL, 17 μL, 18 μL, 19 μL, 20 μL, 21 μL, 22 μL, 23 μL, 24 μL, 25 μL, 30 μL, 35 μL, 40 μL, 45 μL, 50 μL, 55 μL, 60 μL, 65 μL, 70 μL, 75 μL, 80 μL, 85 μL, 90 μL, 95 μL, 100 μL, 200 μL, 300 μL, 400 μL, 500 μL, 600 μL, 700 μL, 800 μL, 900 μL, 1000 μL, or more of the sample may be used. In some cases, the volume of input sample may be between any of the two values described herein.

Assays and Enrichment of Substances

Methods of the present disclosure may comprise one or more assays. An assay may be performed on a biological sample as described above to determine the presence of or detect a substance (e.g., biomolecule or biomarker, such as a protein), to isolate or purify a substance, to quantitate the amount of a substance, to enrich for an amount of a substance, or any combination thereof. In some cases assays may be performed to enrich for one or more substances. Enrichment of a substance may comprise increasing the concentration of a substance in a sample. Alternatively or additionally, enrichment may comprise isolating a target substance from the sample and optionally transferring the isolated target substance to a different medium. The product or output of an assay may comprise one or more isolated and/or purified substances (e.g., biomarkers, proteins). Assayed (e.g., isolated, purified) substances may be subsequently analyzed and/or characterized as part of methods disclosed herein. Alternatively, the output of an assay may comprise the input sample or a portion (e.g., aliquot) thereof.

Assays as described herein may include, but are not limited to, immunoassays, enzyme-linked immunosorbent assays (ELISA), radioimmunoassays (RIA), ligand binding assays, functional assays, enzymatic assays, enzymatic digestions (e.g., by proteases or nucleases), spectroscopic assays (e.g., UV-vis spectroscopy, Fourier transform infrared spectroscopy, circular dichroism spectroscopy) spectrophotometric assays (e.g., ultraviolet-visible light spectrophotometry), immunoprecipitations (IP), sequencing reactions, electrophoresis, chromatography, enrichments, pull-downs, mass spectrometry (MS), and the like. In some cases, the assay may comprise an immunoprecipitation reaction. The immunoprecipitation reaction may be performed to enrich for one or more proteins in a sample. In some cases, a method as described herein comprises not performing one or more assays. In some cases, a method comprises not subjecting proteins to enzymatic cleavage (e.g., by one or more proteases).

In some cases, an assay as described herein may be performed on a sample containing one or more proteins. Proteins assayed by the methods and systems described herein may be proteins associated with a neurodegenerative disease such as Alzheimer's Disease (AD). Proteins associated with AD include β-amyloid (also "amyloid beta", "beta amyloid", or "Aβ") proteins and modified proteins thereof. By way of nonlimiting example, such proteins may include Aβ38, APP669-711, Aβ40, Aβ42, and amyloid precursor protein (APP) and isoforms thereof. Attentively or additionally, proteins associated with AD may include tau proteins ("t proteins" or "Tau") and modifications thereof such as phosphorylated-Tau. In some cases, an IP assay is performed to enrich a sample for one or more proteins associated with AD. In some cases, the proteins are subjected to enzymatic digestion. In some cases, the proteins are not subject to enzymatic digestion.

One or more assays may be performed on a sample. The methods disclosed herein may comprise performing 1, 2, 3, 4, 5, 6, 7, 8, 9, 10, 11, 12, 13, 14, 15, 16, 17, 18, 19, 20, or more assays on a sample. The one or more assays may be performed sequentially or simultaneously. The one or more assays may be performed on the same sample or portions (e.g., aliquots) thereof or they may be performed on different samples.

One subset of assays may serve a different function than another subset of assays. For example, one assay may be performed to determine the presence of a substance in a sample and a second assay may be performed to isolate the substance from the sample. Assays may be performed in any appropriate order. For example, a sample may first be assayed to determine the presence of a target substance. A second assay may then be used to isolate the target substance from the sample. Optionally, a third assay may be performed to purify the isolated substance. In another example, a sample is first assayed to isolate a substance or plurality of substances. A second assay is then performed on the isolate to determine the presence or absence of a target substance or substances in the isolate. Optionally, a third assay is performed between the first and second assays to purify the one or more target substances. In another example, an assay is performed to enrich for the presence or one or more proteins in a sample. Before or after the enrichment step, another assay is optionally performed to determine the presence of the one or more proteins. Still other combinations and sequences of assays on a sample are contemplated herein.

In some cases, a sample is assayed or analyzed by a third party. For example, one party may conduct a purification or enrichment assay on a sample. The purified or enriched sample may then be subjected to a subsequent assay (e.g., a quantitation) by a different party.

Separation of Substances

Methods as described herein may comprise or one more steps of separating substances, such as proteins. The substances may be separated from an unprocessed sample or they may be separated from a sample that has been assayed (e.g., enriched) for one or more substances (e.g., proteins) of interest. The enriched substances may be in the original sample or they may be in a medium separate from the original sample.

The medium comprising the enriched substances (e.g., proteins), or a subset thereof, may be a liquid medium. The liquid medium may be aqueous solution. Alternatively or additionally, the liquid medium may comprise one or more inorganic or organic solvents. Additional solutes or analytes other than the proteins or a subset thereof may be present in the liquid medium. The liquid medium may have a certain volume. In some cases, the volume may be less than about 1000 μL, 900 μL, 800 μL, 700 μL, 600 μL, 500 μL, 400 μL, 300 μL, 200 μL, 100 μL, 90 μL, 80 μL, 70 μL, 60 μL, 50 L, 45 μL, 40 μL, 35 μL, 30 μL, 25 μL, 20 μL, 15 μL, 10 μL, 9 μL, 8 μL, 7 μL, 6 μL, 5 μL, 4 μL, 3 μL, 2 μL, 1 μL, 900 nL, 800 nL, 700 nL, 600 nL, 500 nL, 400 nL, 300 nL, 200 nL, 100 nL, 75 nL, 50 nL, 25 nL, 10 nL, 1 nL, 750 picoliter (pL), 500 pL, 250 pL, 100 pL, 75 pL, 50 pL, 25 pL, 10 pL, 5 pL, 1 pL or less. In some cases, the volume may be more than about 1 pL, 5 pL, 10 pL, 25 pL, 50 pL, 75 pL, 100 pL, 250 pL, 500 pL, 750 pL, 1 nL, 10 nL, 25 nL, 50 nL, 75 nL, 100 nL, 200 nL, 300 nL, 400 nL, 500 nL, 600 nL, 700 nL, 800 nL, 900 nL, 1 μL, 2 μL, 3 μL, 4 μL, 5 μL, 6 μL, 7 μL, 8 μL, 9 μL, 10 μL, 11 μL, 12 μL, 13 μL, 14 μL, 15 μL, 16 μL, 17 μL, 18 μL, 19 μL, 20 μL, 21 μL, 22 μL, 23 μL, 24 μL, 25 L, 30 μL, 35 μL, 40 μL, 45 μL, 50 μL, 55 μL, 60 μL, 65 μL, 70 μL, 75 μL, 80 μL, 85 μL, 90 μL, 95 μL, 100 μL, 200 μL, 300 μL, 400 μL, 500 μL, 600 μL, 700 μL, 800 μL, 900 μL, 1000 μL, or more. In some cases, the volume of the liquid medium may be between any two values described here.

In some cases, individual biomolecules may be separated by a microfluidic device. A microfluidic device can include a set of micro-channels etched or molded into a material (e.g., glass, silicon or polymer etc.). The micro-channels forming the microfluidic device may be connected together in order to achieve a desired function (e.g., mix, pump, transport, direct, redirect and/or allow flow of a substance or a group of substances inside channels). In some cases, the microfluidic device may be a chip (e.g., a single-plex chip, a multi-plex chip). In some cases, the microfluidic device may be part of a chip. A chip may be assembled from a plurality of multiple multi-layer microfluidic devices using manifolds and clamps. The chip may have a feature of disposability or multi-uses. The microfluidic device may be disposable or reusable. For example, in some cases, the microfluidic device may be single use for a single sample or a plurality of samples. In some cases, the microfluidic device may be multi-use for a single sample or a plurality of samples.

The fluid channel may be of different shapes, e.g., cube, cuboid, cone, cylinder, prism, pyramid, or any regular or irregular shapes. In cases where more than one fluid channels are comprised in the device, each of the fluid channels may be of the same or a different shape. In some cases, a certain percentage of the fluid channels may have the same or a different shape, for example, 99% of the fluid channels may have the same shape.

The length of the fluid channel may vary, depending upon, for example, quantity, acidity, basicity, charge, size, architecture, hydrophobicity, hydrophobicity, and affinity of the analyte. In some cases, a longer fluid channel may be preferred. In some cases, a shorter fluid channel may be used. In some cases, the length of the fluid channel may be less than or equal to about 100 centimeters (cm), 75 cm, 50 cm, 25 cm, 20 cm, 18 cm, 16 cm, 14 cm, 12 cm, 10 cm, 9 cm, 8 cm, 7 cm, 6 cm, 5 cm, 4 cm, 3 cm, 2 cm, 1 cm, 0.5 cm, 0.25 cm, 0.1 cm, 0.05 cm, or 0.01 cm. In some cases, the length of the fluid channel may be at least about 0.0001 cm, 0.0005 cm, 0.001 cm, 0.005 cm, 0.01 cm, 0.05 cm, 0.1 cm, 0.5 cm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 18 cm, 20 cm, 25 cm, 30 cm, 35 cm, 40 cm, 50 cm, 60 cm, 70 cm, 80 cm, 90 cm, 100 cm, 200 cm, or more. In some cases, the length of the channel may be between any of two values described herein.

In some cases, the fluid channel may have a cross-section that is of a certain shape, for example, square, triangular, rectangular, circular, polygonal, or any types of regular or random shapes. Dimensions of the cross-section of the fluid channel may vary. For example, the dimension for each side of the shape are less than or equal to about 5000 microns (μm), 4000 μm, 3000 μm, 2000 μm, 1000 μm, 750 μm, 500 μm, 450 μm, 400 μm, 350 μm, 300 μm, 250 μm, 200 μm, 190 μm, 180 μm, 170 μm, 160 μm, 150 μm, 140 μm, 130 μm, 120 μm, 110 μm, 100 μm, 90 μm, 80 μm, 70 μm, 50 μm, 30 μm, 10 μm, 5 μm, 1 μm, or less. In some cases, the dimension for each side of the shape are at least about 1 μm, 5 μm, 10 μm, 25 μm, 50 μm, 75 μm, 80 μm, 90 μm, 100 μm, 110 μm, 120 μm, 130 μm, 140 μm, 145 μm, 150 μm, 160 μm, 170 μm, 180 μm, 190 μm, 200 μm, 250 μm, 300 μm, 350 μm, 400 μm, 450 μm, 500 μm, 750 μm, 1000 μm, or more. In some cases, the dimension for each side of the shape may be between any of the two values described herein. In some examples, the fluid channel may have a cross-section of about 100 μm×100 μm. In some example, the fluid channel may have a cross-section of about 200 μm×200 μm. In some example, the fluid channel may have a cross-section of about 120 μm×300 μm.

As will be appreciated, in some cases, it may be preferred that each of the fluid channels has different dimensions. For example, a separation channel may be designed to be 5 cm×100 μm×100 μm, while the trap column is 1 cm×300 μm×120 μm. In some cases, each fluid channel in the microfluidic device may be of the same dimensions, for example, 4 cm×150 μm×150 μm. In some cases, it may be desired that a certain percentage of the fluid channels are of the same dimensions, e.g., about 5%, 10%, 15%, 20%, 25%, 30%, 35%, 40%, 50%, 60%, 70%, 80%, 90%, or 100% of the fluid channels.

Flow rates for the fluid channels may vary, dependent upon, for example, channel dimensions. For example, a fluid channel with smaller cross-sectional dimensions may require a lower flow rate. For example, a fluid channel with dimensions of 1 cm×300 μm×120 μm may be capable of a flow rate of about 20 microliters (μL)/minute (min), while a fluid channel with dimensions of 5 cm×100 μm×100 μm may only be capable of a flow rate of about 600 nanoliters (nL)/min.

In some cases, the liquid medium may be flowed through the microfluidic device at a certain flow rate. The flow rate may be greater than about 1 picoliter/min (pL/min), 5 pL/min, 10 pL/min, 25 pL/min, 50 pL/min, 75 pL/min, 100 pL/min, 250 pL/min, 500 pL/min, 750 pL/min, 1 nanoliter/min (nL/min), 10 nL/min, 25 nL/min, 50 nL/min, 75 nL/min, 100 nL/min, 200 nL/min, 300 nL/min, 400 nL/min, 500 nL/min, 600 nL/min, 700 nL/min, 800 nL/min, 900 nL/min, 1 μL/min, 2 μL/min, 3 μL/min, 4 μL/min, 5 μL/min, 6 L/min, 7 μL/min, 8 L/min, 9 μL/min, 10 μL/min, 11 μL/min, 12 μL/min, 13 μL/min, 14 L/min, 15 L/min, 16 μL/min, 17 μL/min, 18 μL/min, 19 μL/min, 20 μL/min, 21 μL/min, 22 μL/min, 23 L/min, 24 μL/min, 25 μL/min, 30 μL/min, 35 L/min, 40 μL/min, 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 200 μL/min, 300 μL/min, 400 μL/min, 500 μL/min, 600 μL/min, 700 μL/min, 800 μL/min, 900 μL/min, 1000 μL/min, or more. In some cases, the flow rate may be less than about 1000 μL/min, 900 μL/min, 800 μL/min, 700 μL/min, 600 μL/min, 500 μL/min, 400 μL/min, 300 μL/min, 200 μL/min, 100 μL/min, 90 μL/min, 80 μL/min, 70 μL/min, 60 μL/min, 50 μL/min, 45 μL/min, 40 μL/min, 35 μL/min, 30 μL/min, 25 μL/min, 20 μL/min, 15 μL/min, 10 μL/min, 9 L/min, 8 μL/min, 7 μL/min, 6 L/min, 5 μL/min, 4 μL/min, 3 L/min, 2 μL, 1 μL/min, 900 nL/min, 800 nL/min, 700 nL/min, 600 nL/min, 500 nL/min, 400 nL/min, 300 nL/min, 200 nL/min, 100 nL/min, 75 nL/min, 50 nL/min, 25 nL/min, 10 nL/min, 1 nL/min, 750 pL/min, 500 pL/min, 250 pL/min, 100 pL/min, 75 pL/min, 50 pL/min, 25 pL/min, 10 pL/min, 5 pL/min, 1 pL or less. In some cases, the flow rate may be between any two values described herein.

Various methods or techniques may be used for biomolecule (e.g., protein) separation. Non-limiting examples of methods or techniques may include Column Chromatography, Paper Chromatography, Thin Layer Chromatography, Gas Chromatography, Liquid Chromatography, Supercritical Fluid Chromatography, Ion Exchange Chromatography, Size-exclusion Chromatography, Expanded Bed Adsorption (EBA) Chromatographic Separation, Two-dimensional Chromatography, Simulated moving-bed Chromatography, Pyrolysis Gas Chromatography, Fast Protein Liquid Chromatography, Countercurrent Chromatography, Chiral Chromatography, Capillary Electrophoresis, Capillary Gel Electrophoresis, Capillary Zone Electrophoresis, Capillary Isoelectric Focusing, Capillary Electrochromatography, or combinations thereof. As provided herein, at least one fluid channel may be adapted to separate substances of interest included in a sample, based on one or more of the above-mentioned separation techniques. For example, in some cases, the microfluidic device may comprise at least one fluid channel (or LC-column) to preform Liquid Chromatography on the sample.

In cases where at least one fluid channel is a LC-column, the column comprises a separation medium that is adapted to separate substances included in a sample into subsets of substances along the column when the sample is forced through the channel under high pressure. The separation medium may comprise porous monoliths directly fabricated inside the column, which can be porous rod structures characterized by mesopores and macropores. As an alternative or in addition to, the separation medium may comprise a plurality of particles (e.g., silica particles, polymer particles, sorbents, or beads) with the same or varying sizes, porosity, and functional groups for diverse liquid chromatography (LC) separation including, but not limited to, reverse-phase, ion-exchange, size-exclusion, and hydrophilic interaction liquid chromatography (HILIC). In some cases, all of the particles have the same size. In some cases, each of the particles may have a different size. In some cases, a certain portion of the particles may have the same size. Particle size (or dimensions) may vary, depending upon, for example, column length, separation time, resolution, detection limits, type of eluants used etc. In some cases, the particles may have a size (or cross-sectional dimension) greater than or equal to about 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 17 μm, 19 μm, 20 μm, 30 μm, 40 μm, 50 μm, 60 μm, 70 μm, 80 μm, 90 μm, 100 μm, or more. In some cases, the particle size (or cross-sectional dimension) may be less than or equal to about 300 μm, 200 μm, 150 μm, 100 μm, 90 μm, 80 μm, 70 μm, 60 μm, 50 μm, 40 μm, 30 μm, 25 μm, 20 μm, 18 μm, 16 μm, 14 μm, 12 μm, 10 μm, 8 μm, 7 μm, 6 μm, 5 μm, 4 μm, 3 μm, 2 μm, 1 μm, or less. In some cases, the particle size (or cross-sectional dimension) may be between any of the two values described herein. In some cases, the particles may have a narrow size distribution. In some cases, the particles may have a broad size distribution. For reverse-phase separation, the alkyl chains for the stationary phase may range from C1 (i.e., methyl), to C30, for example, C4, C8, or C18.

Various solvents may be used in LC-analysis, e.g., organic, inorganic, or mixed solvent. Non-limiting examples of solvents may include water, methanol, propanol, acetonitrile, dioxane, ethyl acetate, acetone, diethyl ether, tetrahydrofuran, methylene chloride, chloroform, carbon tetrachloride, isooctane, hexane, or combinations thereof. In some cases, solvent gradient may be required when running LC analysis. Gradients can be linear or non-linear. Gradients can have multiple segments.

The design, fabrication, structure, and applications of a microfluidic device may be as described in, for example, U.S. Pat. Nos. 8,022,361, 9,793,477, and PCT Patent Publication No. WO 2014/093080, each of which is incorporated herein by reference in its entirety.

Detection of Substances

As described elsewhere herein, the present disclosure provides methods and systems for detecting or identifying a presence or absence of one or more of substances (e.g., biomarkers, including cells, proteins, peptides, lipids, small molecules, etc.) in a sample. The detection of the presence or absence of one or more substances may further comprise detecting a presence or absence of one or more subsets of the substances. The substances or the subsets of the substances may be detected by various methods or techniques. The presence or absence of the one or more of substances in the sample may be indicative of a likelihood of a sample being positive for a disease or condition. Non-limiting examples of detectors for use with the methods described herein may include Flame ionization detector (FID), Aerosol-based detector (NQA), Flame photometric detector (FPD), Atomic-emission detector (AED), Nitrogen Phosphorus Detector (NPD), Evaporative light scattering detector (ELSD), Mass spectrometer (MS) (e.g., quadrupole MS, orthogonal MS, etc.), UV detectors (e.g., diode array detector (DAD or PDA)), Thermal conductivity detector (TCD), Fluorescence detector, Electron capture detector (ECD), Conductivity monitor, Photoionization detector (PID), Refractive index detector (RI or RID), Radio flow detector, Chiral detector, or combinations thereof. Examples of detectors that may be used with methods and systems of the present disclosure are found in U.S. Pat. Nos. 8,022,361, 9,793,477, and PCT Patent Publication No. WO 2014/093080, each of which is incorporated herein by reference in its entirety.

Mass Spectrometry (MS) is an analytical technique that can be used for identifying the amount and type of chemicals present in a sample, determining the elemental composition of samples, quantitating the mass of particles and molecules, and elucidating the chemical structure of molecules by measuring the mass-to-charge ratio and the abundance of gas-phase ions. Various types of MS-based technologies with high specificity, such as Liquid Chromatography (LC-MS), Gas Chromatography (GC-MS), and Matrix-Assisted Laser Desorption/Ionization/Time-Of-Flight (MALDI-TOF MS), can be utilized as tools in clinical laboratories for disease screening, diagnosis of disease and metabolic disorders, monitoring of drug therapy, identifying drug toxicity and poisoning, and discovering new biomarkers.

Mass spectrometry-based proteomics can be an indispensable and powerful tool for diagnostics of diseases and monitoring of their progression and therapeutic responses. The focus of clinical proteomics has been on analyzing low-abundance proteins using bottom-up proteomics (i.e., analysis of proteolytic peptides), which faces the challenge of the huge dynamic range in biological fluids such as blood and urine, and the difficulty of identifying all protein isoforms (or proteoforms), including splicing, modifications, cleavages etc., and quantitating their stoichiometry. There have been recent advances in top-down proteomics, i.e., large-scale identification and characterization of full-length proteins, but its clinical potentials remain largely unexplored. The ability of mass spectrometry to identify and, more importantly, to precisely quantitate thousands of proteins from complex samples can be useful in the fields of biology and medicine.

In cases where a MS detector is utilized, the presence or absence of the substances or the subsets of the substances may be detected based on their ionization patterns in the mass spectrometer. The microfluidic device may be configured or adapted to direct at least a portion of the sample via the nozzle to the detector. Electrospray ionization (ESI) is a technique used in mass spectrometry to produce ions. It is especially useful in producing ions from macromolecules (such as proteins) because it overcomes the propensity of these molecules to fragment when ionized. The ions are accelerated under vacuum in an electric filed and separated by mass analyzers according to their m/z ratios. Exemplary mass analyzers include triple-quadrupole, time-of-flight (TOF), magnetic sector, orbitrap, ion trap, quadrupole-TOF, matrix-assisted laser desorption ionization (MALDI) and Fourier transform ion cyclotron resonance (FTICR) analyzers, and the like. As individual ions reach the detector, they are counted. In some cases, the methods disclosed herein comprise using a quadrupole mass spectrometer and/or an orbitrap. In some cases, the methods disclosed herein do not comprise using a MALDI mass spectrometer. The methods as described herein may comprise using signals generated from detection (e.g, generated from MS) to determine the presence or absence of one or more substances in a sample.

Diseases and Physiological Conditions

A variety of diseases, conditions or disorders may be studied, diagnosed and/or monitored by the methods and systems provided in the present disclosure. In some cases, the diseases are neurodegenerative diseases such as Alzheimer's Disease (AD). However, other disease or conditions may be studied, diagnosed and/or monitored using methods and system provided herein. Disease study, diagnosis and/or monitoring can include detecting one or more biomarkers that are indicative of the disease in a sample. In some cases, the sample is derived from a subject. Additionally, the one or more biomarkers may be quantified and used to determine the likelihood that an individual has or diagnose an individual with a disease or condition.

For example, methods and systems provided herein may be used to study, diagnose and/or monitor neoplastic conditions, including, but not limited to, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

Cardiovascular diseases may be studied, diagnosed and/or monitored by methods and systems provided herein. Examples of cardiovascular disease include, but are not limited to, coronary heart disease, ischemic heart disease, cardiomyopathy, hypertensive heart disease, pulmonary heart disease, congestive heart failure, inflammatory heart disease, valvular heart disease, cerebrovascular disease, peripheral arterial disease, congenital heart disease, rheumatic heart disease, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, congestive heart failure, myocardial ischemia, myocardial infarction, cardiac tamponade, myocarditis, pericarditis, arrhythmogenic night ventricular dysplasia, hypertrophic cardiomyopathy, Williams syndrome, heart valve diseases, endocarditis, bacterial, pulmonary atresia, aortic valve stenosis, Raynaud's disease, Raynaud's disease, cholesterol embolism, Wallenberg syndrome, Hippel-Lindau disease, and telangiectasis.

Autoimmune disorders may be studied, diagnosed and/or monitored by the methods and systems provided herein. Examples of autoimmune disorders may include, but not limited to, Crohn's disease, ulcerative colitis, psoriasis, psoriatic arthritis, juvenile arthritis and ankylosing spondilitis, Other non-limiting examples of autoimmune disorders include autoimmune diabetes such as TID, multiple sclerosis, systemic lupus erythematosus (SLE), rheumatoid spondylitis, gouty arthritis, allergy, autoimmune uveitis, nephrotic syndrome, multisystem autoimmune diseases, autoimmune hearing loss, adult respiratory distress syndrome, shock lung, chronic pulmonary inflammatory disease, pulmonary sarcoidosis, pulmonary fibrosis, silicosis, idiopathic interstitial lung disease, chronic obstructive pulmonary disease, asthma, restenosis, spondyloarthropathies, Reiter's syndrome, autoimmune hepatitis, inflammatory skin disorders, vasculitis of large vessels, medium vessels or small vessels, endometriosis, prostatitis and Sjogren's syndrome. Undesirable immune response can also be associated with or result in, e.g., asthma, emphysema, bronchitis, psoriasis, allergy, anaphylaxsis, auto-immune diseases, rhuematoid arthritis, graft versus host disease, transplantation rejection, lung injuries, and lupus erythematosus.

The disease or condition may be an inflammatory condition. The inflammatory condition may be an acute systemic inflammatory disease or a chronic inflammatory disease. Examples of inflammatory conditions may include but not limited to systemic inflammatory response syndrome (SIRS), ARDS, sepsis, inflammatory bowel disease, inflammatory skin diseases, psoriasis, eczema, scleroderma severe sepsis, septic shock erysipelas, meningitis, arthritis, rheumatoid arthritis, toxic shock syndrome, diverticulitis, appendicitis, pancreatitis, cholecystitis, colitis, cellulitis, burn wound infections, pneumonia, urinary tract infections, postoperative infections, peritonitis cystic fibrosis, COPD and other pulmonary diseases, gastrointestinal disease including chronic skin and stomach ulcerations, atopic dermatitis, oral ulcerations, aphtous ulcers, genital ulcerations and inflammatory changes, parodontitis, eye inflammations including conjunctivitis and keratitis, external otitis, mediaotitis and genitourinary inflammations.

Methods and systems provided herein may be utilized for diagnosing and/or monitoring the progression and therapeutic responses of Huntington's Disease, Parkinson's Disease, Alzheimer's disease (AD) or any other neurodegenerative diseases including but not limited to Alexander's disease, Alper's disease, ataxia telangiectasia, Batten disease, bovine spongiform encephalopathy, Canavan disease, Cockayne syndrome, corticobasal degeneration, Creutzfeldt-Jakob disease, HIV-associated dementia, Kennedy's disease, Krabbe's disease, lewy body dementia, Machado-Joseph disease, multiple sclerosis, multiple system atrophy, narcolepsy, neuroborreliosis, Pelizaeus-Merzbacher Disease, peripheral neuropathy, Pick's disease, primary lateral sclerosis, prion diseases, Refsum's disease, Sandhoffs disease, Schilder's disease, subacute combined degeneration of spinal cord secondary to pernicious anaemia, schizophrenia, spinocerebellar ataxia, spinal muscular atrophy, Steele-Richardson-Olszewski disease, and tabes *dorsalis*.

Determination of Diseases or Conditions

The methods as disclosed herein may further comprise determining a likelihood that a biological sample is positive for a disease or condition. For example, signals detected as described above may be used to quantitate an amount (e.g., concentration, mass, molar amount) of one or more biomarkers (e.g., proteins, lipids) present in the biological sample or portion thereof. Based on the quantification, a diagnosis of or likelihood of the biological sample being positive for a disease or condition may be made. The determination of likelihood may be made by comparing the quantified value of one or more biomarkers (e.g., a ratio of quantities of two or more proteins) to see if they are above or below a certain threshold. In some cases, a ratio or other expression (e.g., a rational expression) of amounts of more than one biomarker may be compared to a cutoff or threshold value.

A cutoff or threshold value may be determined by analyzing one or more references samples. References samples may comprise biological samples or parts thereof as described herein that are known to be positive for a certain disease or condition. The cutoff value may be determined by calculating a test statistic characterizing the performance of a biomarker or combination of biomarkers (e.g., a ratio of biomarkers) at correctly classifying the test data. In some cases, the test statistic may be Youden's Index, F-score, Matthews Correlation Coefficient, phi coefficient, Cohen's kappa, and the like. Alternatively or additionally, a cutoff may be selected to have a certain specificity, sensitivity, or some combination thereof. In an example, the threshold or cutoff value for a certain biomarker or set of biomarkers may be determined by constructing a receiver operating characteristic curve, and the cutoff is selected as the value which gives the maximal Youden's Index for the curve. The reference data may comprise quantified biomarker data from a set of biological samples. Various biomarkers and combinations thereof may be tested to determine which biomarker or set(s) of biomarkers is the most accurate or otherwise optimal (e.g., as determined by receiver operating characteristic analysis) for determining a likelihood or diagnosis.

In some cases, the quantified value or ratio or rational expression of quantified values comprise a ratio of Aβ42 and Aβ40, or a ratio of APP669-711 and Aβ42. The quantified value or ratio or rational expression of quantified values may be above a certain cutoff. The cutoff value may be great or equal to about 0.001, 0.01, 0.015, 0.02, 0.025, 0.03, 0.0.35, 0.04, 0.045, 0.05, 0.055, 0.06, 0.065, 0.07, 0.075, 0.085, 0.09, 0.095, 0.1, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.3, 0.4, 0.5, 0.6, 0.7, 0.8, 0.9, 1.0, 2.0, 5.0, 10.0, 25.0, 50.0, 75.0, 100, 250, 750, 1000, or more. The cutoff value may be less than or equal to about 1000, 750, 250, 100, 75.0, 50.0, 25.0, 10.0, 5.0, 2.0, 1.0, 0.9, 0.8, 0.7, 0.6, 0.5, 0.4, 0.3, 0.29, 0.28, 0.27, 0.26, 0.25, 0.24, 0.23, 0.22, 0.21, 0.20, 0.19, 0.18, 0.17, 0.16, 0.15, 0.14, 0.13, 0.12, 0.11, 0.1, 0.095, 0.09, 0.085, 0.08, 0.075, 0.07, 0.065, 0.06, 0.055, 0.05, 0.045, 0.04, 0.035, 0.03, 0.025, 0.02, 0.015, 0.01, 0.001 or less. The cutoff value may lie between any two of these numbers.

A likelihood or diagnosis may be determined by quantifying 1, 2, 3, 4, 5, 6, 7, 8, 9, 10, 11, 12, 13, 14, 15, 16, 17, 18, 19, 20, 50, 100, or more biomarkers. The likelihood or diagnosis may be determined by taking a ratio of two biomarkers and comparing the ratio to a cutoff value. In some cases, the likelihood or diagnosis may be made by evaluating a rational expression of amounts of more than two biomarkers and comparing the value of the rational expression to a cutoff value. In some cases, the likelihood or diagnosis may be determined by the presence of one or more biomarkers. In some cases, the likelihood or diagnosis may be determined by the absence of one or more biomarkers.

In some cases, determining a likelihood (including an increase or decrease thereof) comprises a likelihood of one or more of: a poor clinical outcome, good clinical outcome, high risk of a condition or disease, low risk of a condition or disease, complete response, partial response, stable disease, non-response, and recommended treatments for disease management.

By way of nonlimiting example, the likelihood of a biological sample as being positive for a neurodegenerative disease may be determined by comparing a ratio of two biomarkers to a cutoff value (e.g., threshold). In some cases, the biomarkers are proteins. In some cases, the proteins are proteins associated with a neurodegenerative disease, such as Alzheimer's Disease. By way of nonlimiting example, such proteins may include β-amyloid proteins such as Aβ38, APP669-711, Aβ40, and Aβ42, and tau proteins and derivatives thereof. In some cases, a likelihood or diagnosis of the biological sample as being positive for Alzheimer's Disease or may be made by comparing an amount of Aβ38, APP669-711, Aβ40, or Aβ42 in a biological sample from the subject to a predetermined threshold. Alternatively or additionally, the determination may be made by comparing a ratio or rational expression comprising two or more of Aβ38, APP669-711, Aβ42, or Aβ42 to a predetermined cutoff. In some cases, the determination may be made by comparing a ratio of Aβ42/Aβ40 to a predetermined cutoff. In some cases, the subject may be diagnosed or determined as likely to have or be predisposed toward Alzheimer's Disease is the ratio of Aβ42/Aβ40 is below a certain threshold. In some cases, the threshold is between about 0 and about 0.1770. In some cases, the threshold is about 0.1485. In some cases, the determination may be made by comparing a ratio of APP669-711/Aβ40 to a cutoff value. In some cases, the subject may be diagnosed or determined as likely to have or be predisposed toward Alzheimer's Disease is the ratio of APP669-711/Aβ40 is above a certain value.

In some cases, a biomarker or combination of biomarkers (e.g., a ratio or rational expression of biomarkers) may identify the likelihood of a subject having a disease or physiological condition at high accuracy. In some cases, the accuracy may be about 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, 99.9%, or higher. An accuracy may be determined by, for example, comparing a likelihood as determined from a binary classifier to a likelihood as determined by a ground truth or gold standard test for a certain condition or disease. In some cases, a biomarker or combination of biomarkers (e.g., a ratio or rational expression of biomarkers) may identify the likelihood of a subject having a disease or physiological condition with an area under the receiver operating characteristic curve (AUROC). In some cases, the AUROC may be about 0.50, 0.6, 0.70, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 0.999, or higher. In some cases, the disease or physiological condition is a neurodegenerative disease. In some cases, the neurodegenerative disease is Alzheimer's Disease. In some cases, the accuracy is determined by comparing the diagnosis as determined by the set of quantified biomarkers with the diagnosis as determined by amyloid positron emission tomography (amyloid PET).

In some cases, the determination of a biological sample as being positive or likely to exhibit a disease or physiological condition may be used to diagnose or determine a likelihood of the subject from which the sample was derived as having the disease or physiological condition. In some cases, the determination of a biological sample as being positive or likely to exhibit a disease or physiological condition is not used to diagnosis a subject as having a disease or health condition.

Methods as disclosed herein may comprise generating one or more reports that are indicative of the presence or absence of one or more substances in a sample. The one or more reports may be indicative of the quantities of one or more substances in a sample. In some cases, the report may provide a prediction, diagnosis, and/or prognosis of one or more diseases or health conditions. The one or more reports may comprise a risk of having or developing a disease or condition, status of a disease or condition, prognosis of a disease or health conditions, change in disease or health state, and the like. A therapeutic intervention may be provided upon determining the likelihood of a sample and/or subject as being positive for a disease or health condition. Non-limiting examples of therapeutic interventions include pharmaceutical compositions, food and diet-based remedies, nutritional supplements, movement based therapies, surgeries, mental and/or cognitive therapies, electro-stimulation therapy, radiation therapy, respiratory therapy, exercise/activity based therapy, phototherapy, and the like. A therapy may be chosen based on the identified disease or health condition in the sample and/or subject.

Computer Control System

Figure 7:
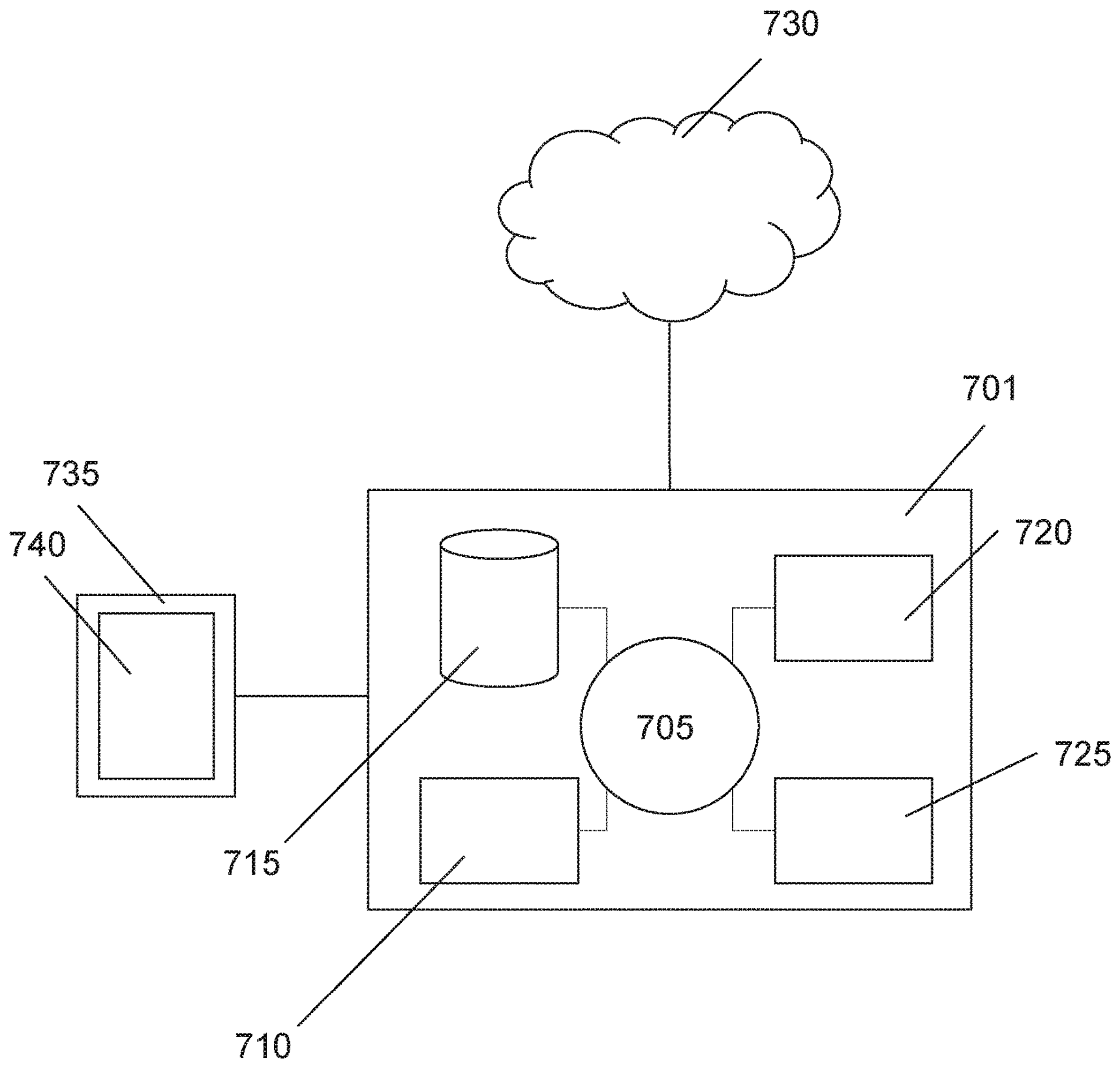
FIG. 7 shows a computer control system that is programmed or otherwise configured to implement methods provided herein.

The present disclosure provides computer control system that is programmed to implement methods of the disclosure. FIG. 7 shows a computer system 701 that is programmed or otherwise configured to facilitate microfluidic chip operation, sample collection, preparation, processing, loading, separation, detection, and/or data analysis. The computer system 701 can regulate various aspects of sample collection, preparation, processing, loading, separation and/or detection of the present disclosure, such as, for example, loading a sample into the microfluidic device, directing the sample through the fluid channels in the device for sample separation, directing the separated sample from the microfluidic device to the detection module, and determining the likelihood of a sample being positive for a disease or health condition. The computer system 701 can be intergraded with the systems provided in the present disclosure.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., a physician, a nurse, a healthcare provider, a patient). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for enabling the user to instruct the computer system 701 to begin sample collection, preparation, processing, loading, separation, detection and/or quantitation. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 705. The algorithm can, for example, implement the general operation of a system for sample collection, preparation, processing, loading, separation, detection and/or quantitation.

Examples

Example 1: Microflow LC-MS for Separating Amyloid Proteins

Figure 1A:
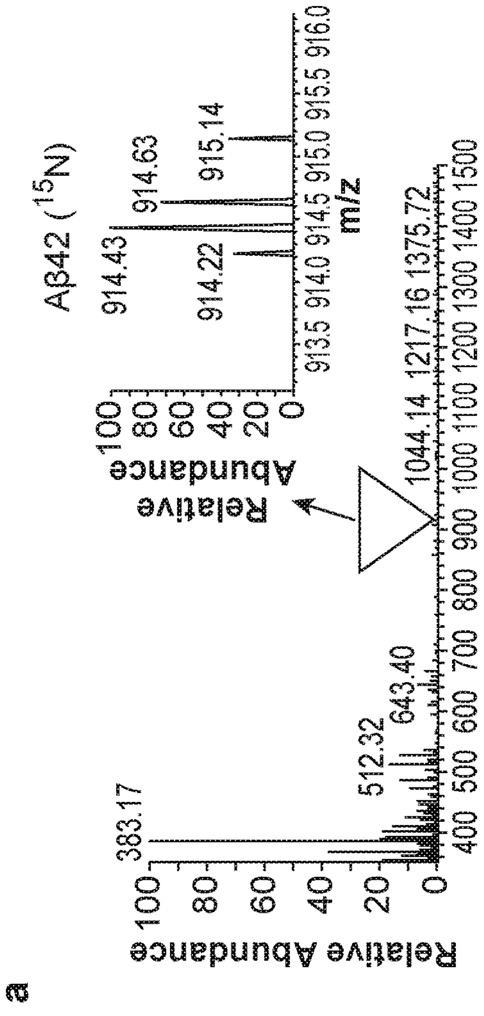
FIG. 1A depicts a full scan MS1 mass spectrum at the apex of the elution profile. The insert shows a zoom-in view of $^{15}$N Aβ42 with missing isotopic peaks.
Figures 2A, 2B, 2C, 2D, 2E, 2F:
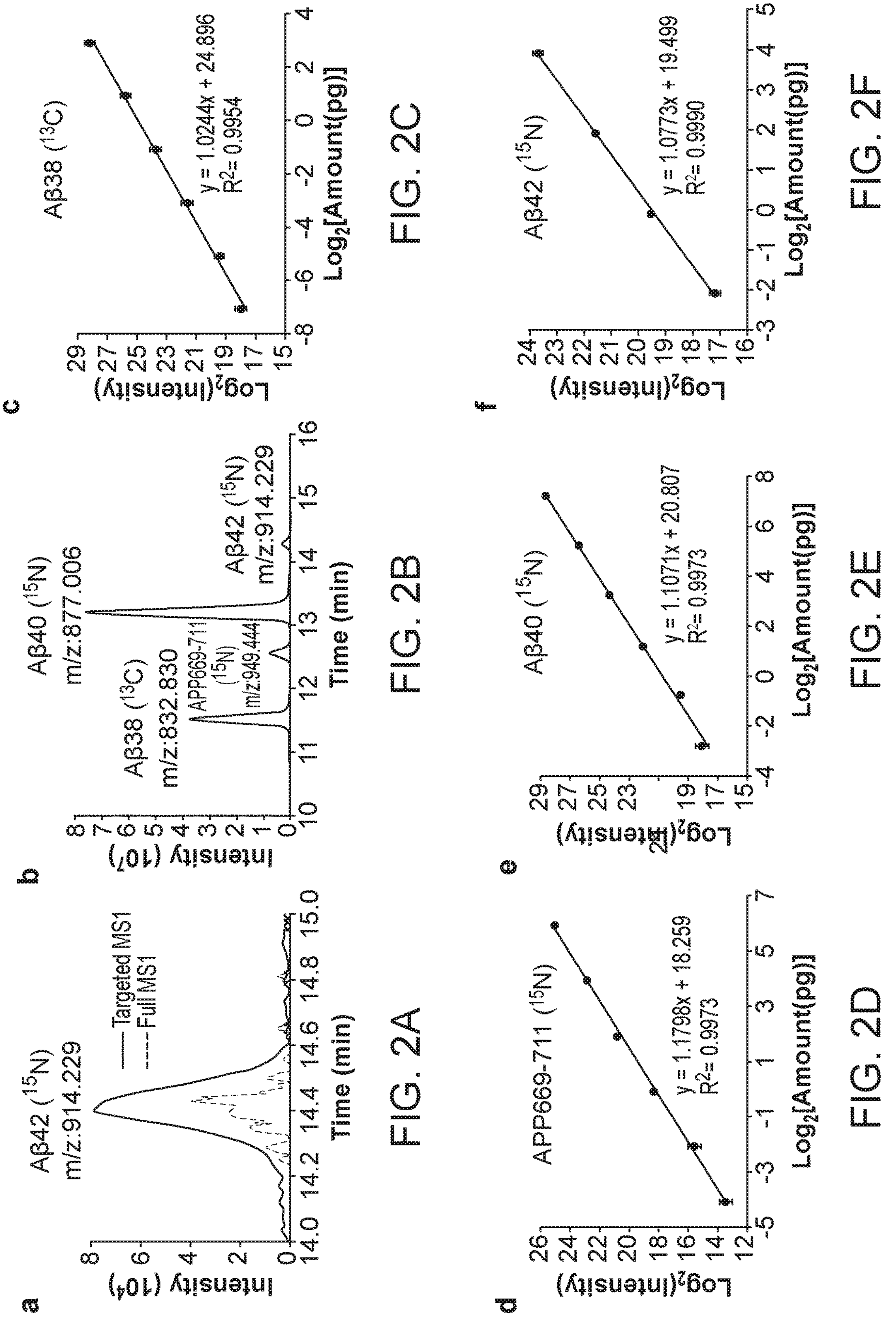
FIG. 2A illustrates a comparison of the analytical performance of targeted and full scan MS1 analyses. Solid and dotted peaks indicate the Extracted Ion Chromatograms of $^{15}$N Aβ42 using targeted and full scan MS1 methods, respectively. 0.94 μg $^{15}$N Aβ42 and 750 ng BSA matrix were loaded on column.
FIG. 2B illustrates extracted ion chromatograms of $^{13}$C and $^{15}$N Aβ proteins using targeted MS1 analysis. m/z indicates the monoisotopic mass to charge ratio of the most abundant charge state (5+) of the Aβ proteins analyzed. 7.5 μg $^{13}$C Aβ38, 60 μg $^{15}$N APP669-711, 150 μg $^{15}$N Aβ40, 15 μg $^{15}$N Aβ42, and 750 ng BSA matrix were loaded on column.
FIGS. 2C-2F illustrate a limit of quantification analysis of Aβ proteins. The mean signal intensities from four replicates and the corresponding amount of Aβ proteins were transformed into log 2 scale. Error bars represent the stand errors of means. The linearities were evaluated with the coefficient of determination ($R^2$). A limit of quantification of 0.06 μg for Aβ38 (FIG. 2C), 0.94 μg for APP669-711 (FIG. 2D), 0.59 μg for Aβ40 (FIG. 2E), and 0.23 μg for Aβ42 (FIG. 2F) were obtained.

A microflow liquid chromatography-target mass spectroscopy (LC-target MS) method was developed to rapidly separate amyloid proteins and determine the relative abundance of their different charge states. The most abundant charge state (5+) of the amyloid proteins was then selected for targeted high resolution MS1 analysis with a predefined m/z range of 3 Thomson (Th) and retention time window. The representative full scan MS1 spectrum (m/z range from 350 to 1,500) and targeted MS1 spectrum of $^{15}N$ Aβ42 are shown in FIG. 1A and FIG. 1B, respectively. As demonstrated in FIGS. 2A, targeted MS1 is more sensitive and exhibits better linearity for amyloid proteins at low concentrations, compared to full scan MS1 (m/z range from 350 to 1,500).

Example 2: Multiplex MS1 Assay for Amyloid Proteins for Diagnosing AD

A multiplex target MS1 assay was developed for four standard $^{13}C$ or $^{15}N$ labeled amyloid proteins for Alzheimer's Disease (AD) diagnosis: Aβ38, APP669-711, Aβ40, and Aβ42. A series of dilutions (4-fold) of a mixture of the proteins was conducted to determine their limit of quantification. The four amyloid proteins were well separated from each other using the micro-flow LC, as demonstrated by the distinct peaks in the chromatogram depicted in FIG. 2B. Good linear correlations were shown between the amounts of amyloid proteins loaded and the peak area intensity from targeted MS1, with the coefficient of determination ($R^2$)

above 0.995 for all four proteins, as illustrated in FIGS. 2C-F. The Limit of quantification (LOQ) was determined at a minimal signal to noise ratio (S/N) of 10, with a Coefficient of Variation (CV) of less than 20% within the linear range. A LOQ of 0.06 μg for Aβ38, 0.94 μg for APP669-711, 0.59 μg for Aβ40 and 0.23 μg for Aβ42 was obtained for they.

Example 3: Microflow LC-Targeted MS1 Analysis of AB Proteins in Plasma

Figure 3A:
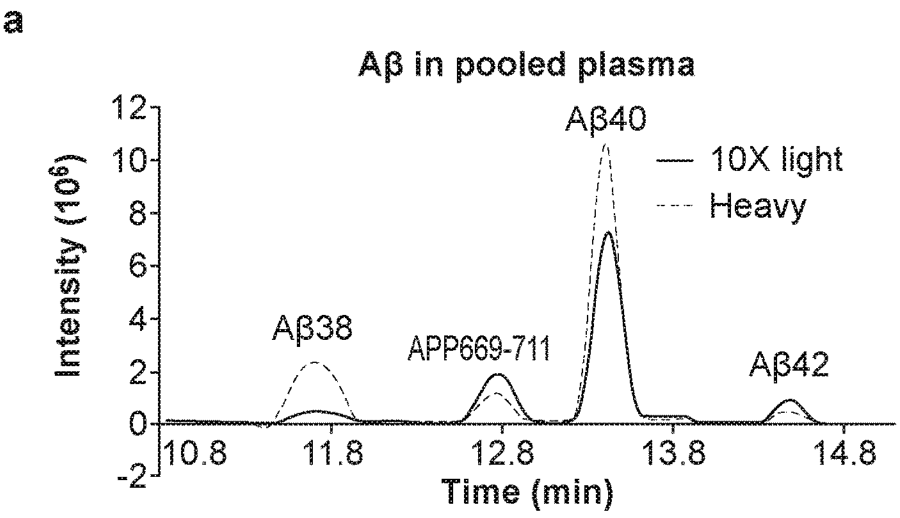
FIG. 3A depicts extracted ion chromatograms of Aβ proteins from plasma IP. 10× light: 10 times of the signals from endogenous proteins from the pooled plasma sample. Heavy: signals from the isotopically labeled proteins that were spiked into the plasma samples before IP.
Figure 3B:
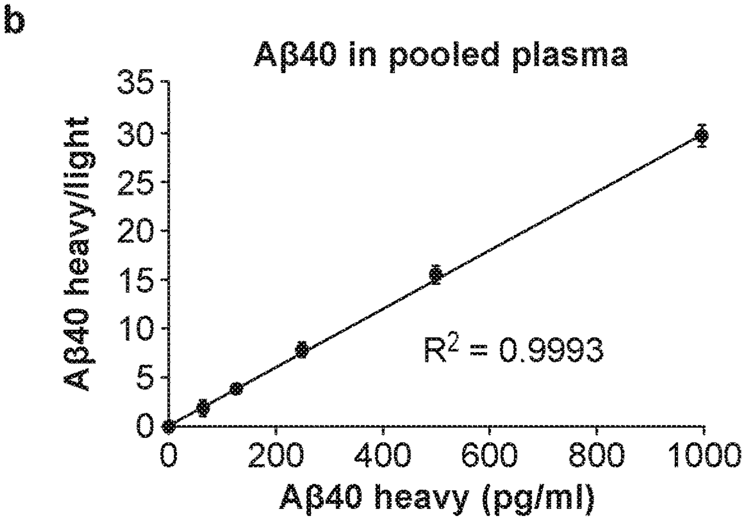
FIGS. 3B-3C depict linear responses of the intensity ratio of heavy/light plot with the amount of heavy protein spiked into the pooled plasma for Aβ40 and Aβ42, respectively. Error bars represent stand errors of means from three repeated injections.
Figure 3C:
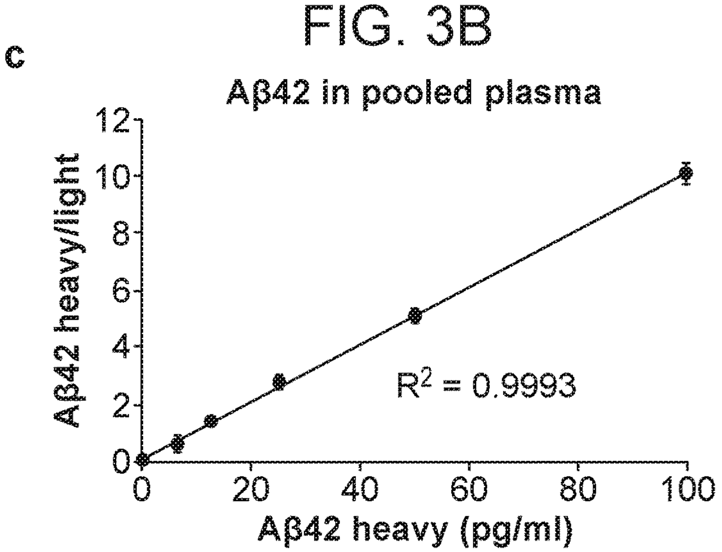
Figure 4A:
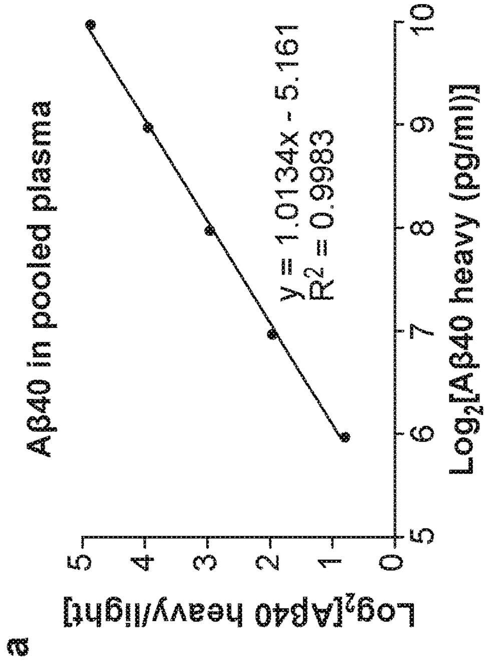
FIGS. 4A-4B depict log 2 plotted data of targeted MS1 analysis of Aβ proteins in plasma corresponding to FIGS. 3B-C, respectively. Error bars represent standard errors of means. The slopes of the linear regression lines for both Aβ40 and Aβ42 are close to 1.
Figure 4B:
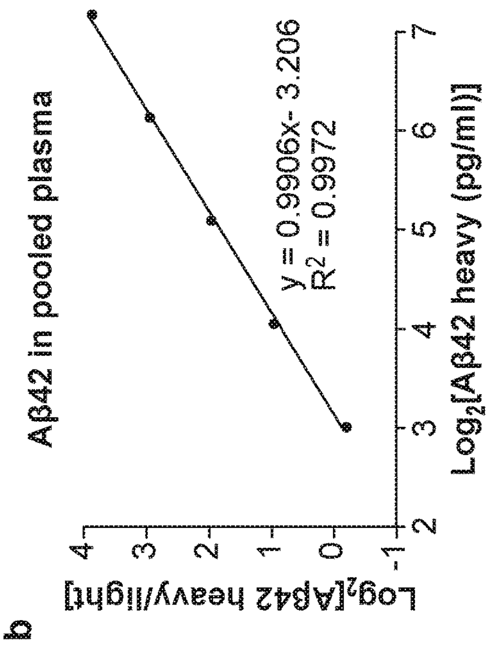
Figure 4C:
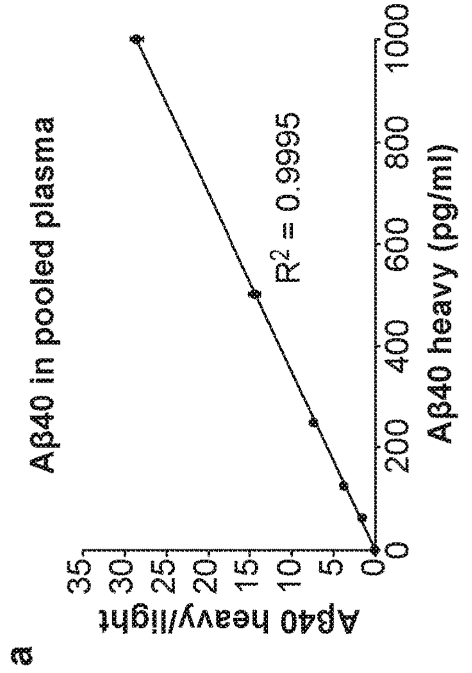
FIGS. 4C-4D depict log 2 plotted data of targeted MS1 analysis of Aβ proteins from aliquots of the plasma AB proteins IP samples used in FIGS. 4A-B that were re-run on the same column after one week. Error bars represent stand errors of means from three repeated injections.
Figure 4D:
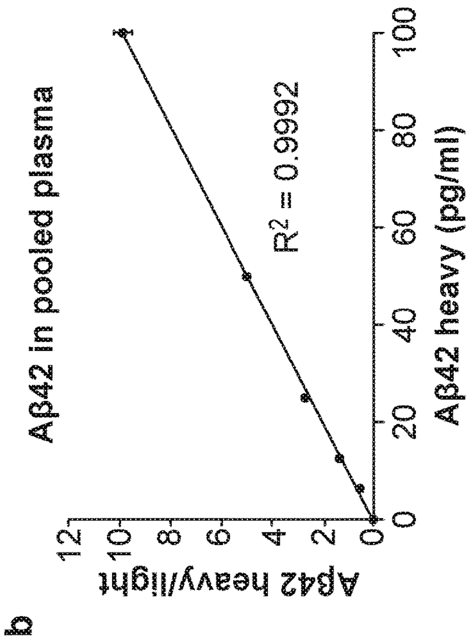

An amyloid proteins immunoprecipitation (IP)-target MS1 method using commercial pooled plasma was developed. The four isotopically labeled amyloid proteins discussed in Example 2 were spiked into 1 mL plasma samples before IP for precise quantification of endogenous proteins. For MS analysis, the endogenous and labeled amyloid proteins were targeted sequentially in a single LC run as illustrated in FIG. 3A. Over 25% IP efficiency was achieved for plasma amyloid proteins based on the recovery of the spiked labeled proteins after IP. To determine the linearity of the plasma AB IP-MS analysis, various concentrations of isotopically labeled amyloid proteins covering the physical concentration ranges were spiked into aliquots of the pooled plasma (containing the same fixed amounts of endogenous light amyloid proteins) and the MS intensity ratio of heavy/light was quantified for each sample. A linear response between the amounts of labeled amyloid proteins spiked in and the ratio of heavy/light peak area intensity from targeted MS1 analysis was obtained, with the coefficient of determination ($R^2$) above 0.999 for both Aβ40 and Aβ42, as illustrated in FIGS. 3B-C. The CV of the intensity ratios from the lowest to the highest spiked concentrations for Aβ40 was 4.3%, 1.1%, 1.2%, 2.5% and 1.6%, respectively; and the corresponding CV for Aβ42 was 14.0%, 3.7%, 1.6%, 1.8% and 2.7%, respectively. The data were plotted using a log 2 scale, and the slopes of the linear regression lines for both Aβ40 and Aβ42 were very close to 1, as shown in FIG. 4A-B, indicating that the MS intensity ratio of heavy/light for both Aβ40 and Aβ42 accurately reflects the actual concentration ratio in the samples. The data reproducibility across multiple days was confirmed by additional experiments performed a week later on aliquots of the same plasma samples run on the same column (FIG. 4C-D).

To assess the reproducibility of the IP-targeted MS1 assay, the same amount of aliquoted isotopically-labeled amyloid proteins was spiked into three individual tubes (1 mL each) of pooled human plasma samples, and IP-MS was performed in parallel. The endogenous amyloid proteins in each tube were quantified by normalizing them to the corresponding spiked-in labeled amyloid protein. The average concentrations of plasma Aβ were 32.2 μg/ml for Aβ40 and 9.3 μg/ml for Aβ42, respectively, and Aβ42/Aβ40 was 0.288, for the pooled commercial plasma. The CV for Aβ40, Aβ42, and Aβ42/Aβ40 was 1.4%, 3.1%, and 2.4%, respectively, as illustrated in Table 1. High resolution (to resolve isotopic peaks) and mass accuracy (typically less than 5 ppm) are necessary for accurate quantification at MS1. Interference peaks that show similar m/z to some isotopic ions of Aβ42 with 5+ charge state were detected, so only the isotopic ions from [M+2] to [M+4] were quantified for Aβ42.

TABLE 1

Reproducibility analysis of IP-MS assay of plasma Aβ proteins

| Replicate | Aβ42 (pg/ml) | Aβ40 (pg/ml) | Aβ42/Aβ40 |
|---|---|---|---|
| 1 | 9.1 | 31.7 | 0.288 |
| 2 | 9.1 | 32.4 | 0.281 |
| 3 | 9.6 | 32.5 | 0.295 |
| Mean | 9.3 | 32.2 | 0.288 |
| SD | 0.29 | 0.44 | 0.007 |
| CV (%) | 3.1 | 1.4 | 2.4 |

Example 4: Prospective Clinical Study

Figure 5A:
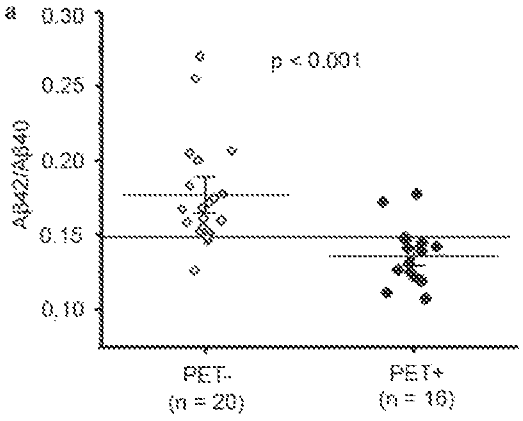
FIG. 5A illustrates Aβ42/Aβ40 decreased in amyloid PET positive individuals. Error bars represent 95% confidence intervals for the mean Aβ42/Aβ40. There were 36 individuals participating in the prospective clinical study, including 20 PET− and 16 PET+ ones. The horizontal line indicates a cutoff of 0.1485.
Figure 5B:
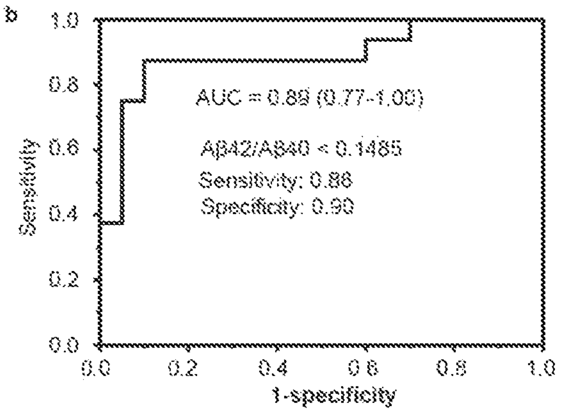
FIG. 5B shows a receiver operating characteristic analysis which demosntrates that plasma Aβ42/Aβ40 was predictive of amyloid PET status. The area under the curve (AUC) is noted with 95% confidence intervals. For the cutoff listed, 88% sensitivity and 90% specificity were achieved. The horizontal line indicates a cutoff of 0.1485.
Figure 5C:
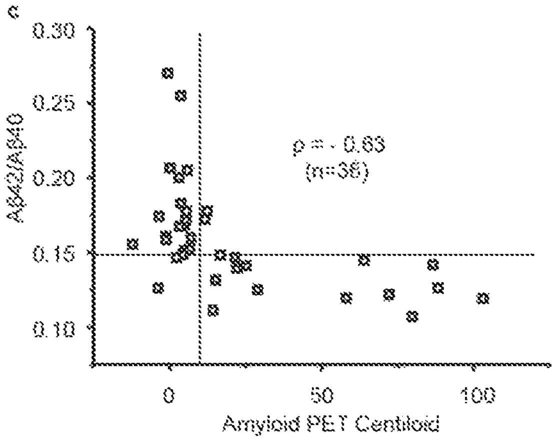
FIG. 5C illustrates Aβ42/Aβ40 may be inversely correlated with amyloid PET status as measured on the Centiloid scale (L shape). The spearman p value is noted. The vertical line indicates a cutoff of 10.
Figure 5D:
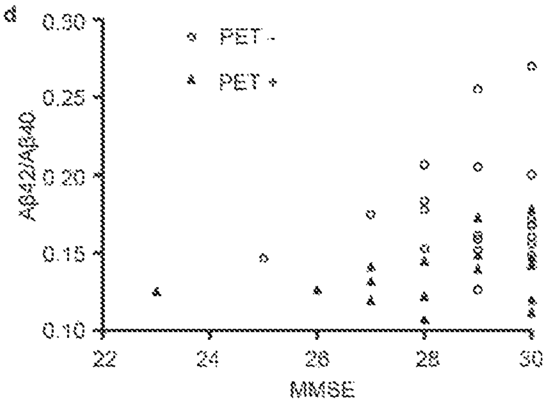
FIG. 5D illustrates a relationship between plasma Aβ42/Aβ40 value and MMSE rating. Individual amyloid PET status was specified. Among participants with a normal MMSE value, a high percentage with low plasma Aβ42/Aβ40 and positive PET was identified.
Figure 6:
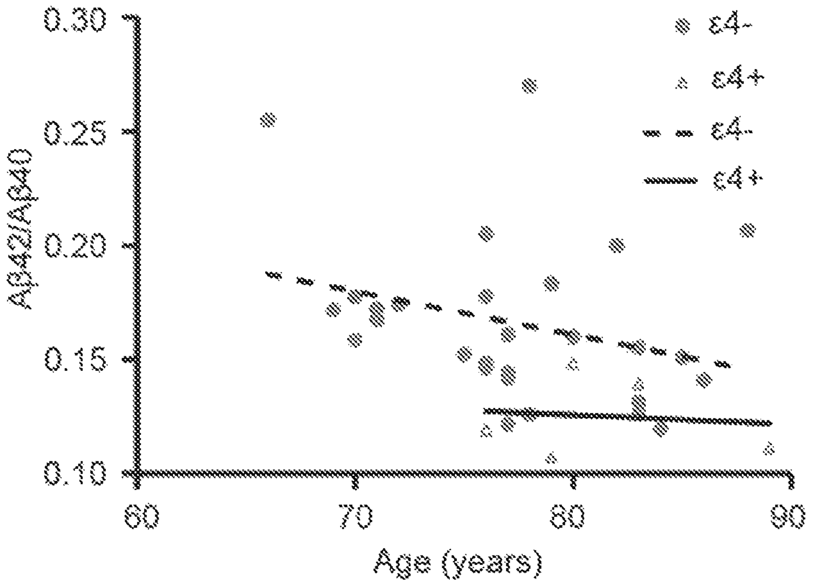
FIG. 6 illustrates a relationship between Aβ42/Aβ40 values and age, with different APOE ε4 status. Plasma Aβ42/Aβ40 was lower with older age (Spearman $\rho=-0.33$, $p=0.08$) and even lower in APOE ε4 carriers. Three individuals had missing APOE ε4 status.

The microflow LC-targeted MS1 assay for amyloid proteins described in Examples 2 and 3 was validated using plasma samples from 36 cognitively normal individuals in a prospective clinical study (Table 2). The same amount of aliquoted isotopically labeled amyloid proteins was spiked into 1 mL of each plasma sample before IP, and 12.5% of the IP products was loaded for each LC-MS replicate run. The endogenous amyloid proteins were quantified by normalizing them to the corresponding labeled amyloid proteins spiked in. An average concentration of 329.5 μg/ml for Aβ40 and 48.0 μg/ml for Aβ42 was obtained for these 36 individuals. Furthermore, all individual concentrations were within the linear ranges for the assay. The ratio of plasma Aβ42/Aβ40 was calculated for each individual, and the result was compared to the data obtained from a brain amyloid PET scan. The CVs of Aβ42/Aβ40 for majority of the IP samples are within 5%. It was found that individuals with a positive amyloid PET had a significantly lower plasma Aβ42/Aβ40 as compared to individuals with a negative amyloid PET (mean=0.1359 vs. 0.1770, $p<0.001$), as shown in FIG. 5A. Receiver Operating Characteristic (ROC) analysis demonstrated that plasma Aβ42/Aβ40 was a good predictor of brain amyloid PET status, with an Area Under Curve (AUC) of 0.89 [95% Confidence Interval (CI) 0.77-1.00], as illustrated in FIG. 5B. A plasma Aβ42/Aβ40 cutoff of <0.1485 was considered positive and had the maximum Youden Index with an accuracy close to 90%. Plasma Aβ42/Aβ40 was inversely corelated with amyloid PET on the Centiloid scale, as shown in FIG. 5C with a Spearman $\rho=-0.63$. There were 2 individuals with positive plasma Aβ42/Aβ40 and negative PET scans, and 2 individuals with negative plasma Aβ42/Aβ40 and positive PET scans; 1 of these individuals was within 5% of the threshold values. Also observed was lower plasma Aβ42/Aβ40 values for older age and in APOE ε4 carriers, as showin in FIG. 6. In addition, a high percentage of cognitively normal individuals has both a low plasma Aβ42/Aβ40 value and corresponding positive PET status, even though majority of them have a normal Mini-Mental State Examination (MMSE), as shown in FIG. 5D. Our data support the notion of affordable rapid screening of the older population, particularly those at risk of AD dementia, by measuring their plasma Aβ42/Aβ40 values.

In conclusion, a microflow-LC targeted MS1 assay for multiplex analysis of intact amyloid proteins from human plasma IP samples was developed. It has been demonstrated high diagnostic accuracy for brain amyloid pathology using our assay in a prospective clinical study.

Methods

Participants

Thirty-six cognitively normal older participants were recruited from the Berkeley Aging Cohort Study (BACS).

All individuals underwent blood draws immediately prior to amyloid and tau PET imaging at Lawrence Berkeley National Laboratory. Participants also underwent clinical assessments that included detailed cognitive testing, the Mini-Mental State Examination (MMSE, Table 1) was a measure of overall cognitive ability.

TABLE 1

| Participant Characteristics | Participants (N = 36) |
|---|---|
| Age (years) | 78 (6) |
| Education (years) | 17 (2) |
| Sex (F/M) | 19/17 |
| MMSE | 29 (1.6) |
| APOE4 carriers | 5* |
| PiB DVR | 1.142 (0.215) |
| PiB Centiloid | 21 (31) |
| PIB positive/negative | 16+/20− |

All values are mean (SD)
MMSE: Mini-Mental State Examination
* 3 missing

Plasma Collection and Processing

At the same session of brain imaging, blood was drawn into one 10 ml tube precoated with $K_2EDTA$ (BD cat #366643). The samples were centrifuged to separate plasma from blood cells within two hours of phlebotomy. The plasma was then aliquoted into 0.5 ml each in a low protein-binding tube (Eppendorf cat #022431081) and stored at −80° C.

Immunoprecipitation of Amyloid Proteins from Plasma

Endogenous amyloid proteins (Aβ38, APP669-711, Aβ40 and Aβ42) were simultaneously immunoprecipitated from a 1 ml of plasma at 4° C. using a monoclonal antibody (6E10 from Biolegend, cat #803003) conjugated to the M-270 Epoxy Dynabeads® (Thermo Fisher Scientific, cat #14302D). A volume of 125 μl 5× master mix containing 2.5× phosphate-buffered saline (PBS), 1% n-nonyl-β-D-thiomaltoside (NTM), 1% n-dodecyl-β-D-maltoside (DDM) and 5× complete protease inhibitor cocktail from Roche was added into each 500 μl plasma sample. Two 0.5 ml plasma samples from each individual were thawed at 4° C. and combined. The total 1 ml of plasma was spiked with 5 μl solution containing 10 pg/μl $^{13}C$ Phe & Ile Aβ38 (AnaSpec™, cat #AS-65220), 40 pg/μl $^{15}N$ APP669-711, 100 pg/μl $^{15}N$ Aβ40, and 10 pg/μl $^{15}N$ Aβ42 (Rpeptide®, cat #AP-1101-1, A-1101-1 and A-1102-1 respectively), with 500 ng/μl BSA as matrix in 10% acetonitrile (ACN), 5% methanol, and 0.2% formic acid (FA). The plasma amyloid proteins and internal standard were immunoprecipitated by incubating 0.5 mg antibody beads with the plasma overnight at 4° C. The beads after IP were washed twice with 1×PBS, three times with 50 mM (NH4)2CO3, and one time with 10 mM (NH4)2CO3. Proteins bound to the beads were then eluted with 60 μl 70% ACN elution buffer containing 5 mM HCl and 100 ng/μl BSA. Finally, eluted proteins were transferred to a new low protein-binding tube, dried under vacuum, and stored at −80° C. before LC-MS analysis.

LC-MS Analysis of Plasma IP Samples

Dried amyloid proteins were reconstituted with 24 μl of 10% ACN, 5% methanol and 0.2% FA. After the undissolved pellet was spun down, amyloid proteins in the supernatant were transferred to a sample vial. For each technical replicate, a 3 μl aliquot was subjected to liquid chromatography mass spectrometry (LC-MS) analysis on a Thermo Orbitrap Q-Exactive Plus Mass Spectrometer interfaced with a Thermo Dionex® 3000 HPLC system. Samples were loaded via a 20 μl sample loop onto a Waters 150 μm×100 mm nanoEase M/Z Protein BEH C4 column using 95% buffer A (3% ACN and 0.2% FA) and 5% buffer B (97% ACN and 0.2% FA) for 5 min. The column was placed in a column heater set at 50° C. with a constant 1.5 μl/min flow rate. Proteins were then resolved using a steep 1.9-minute gradient from 5% B to 20% B, followed by a 11-minute linear gradient from 20% buffer B to 32% buffer B, then followed by a 2 min gradient to 50% B. Unresolved proteins were then washed off the column with 95% B for 3 min. The column was then re-equilibrated with 5% B for 5 min.

Proteins eluted from the column were ionized using a Thermo Nanospray Flex ion source with a stainless-steel emitter. A 275° C. capillary temperature and 60% of S-lens RF level were used. For targeted MS1 analysis, the m/z of the most abundant charge state of amyloid proteins (5+ for both light and heavy labeled proteins) were selected at the expected retention time with a 3-Thomson (Th) isolation window (0.4 Th offset) and automatic gain control (AGC) values of $1e^5$. Maximum fill time for each protein was 400 ms, and Orbitrap resolution was 70,000. Table 3 lists the details of the MS parameters for each protein analyzed.

TABLE 3

MS parameters for targeted MS1 analysis of Aβ proteins

| Protein name | Target m/z | Isolation m/z range | CS [z] | Start [min] | End [min] | Peak Retention Time [min] | Total MS intensity (Area) |
|---|---|---|---|---|---|---|---|
| Aβ38 | 827.21 | 825.71-828.71 | 5 | 10 | 12.4 | 11.36 | 4291448 |
| Aβ38 ($^{13}C$) | 833.23 | 831.73-834.73 | 5 | 10 | 12.4 | 11.36 | 18417822 |
| APP669-711 | 938.48 | 936.98-939.98 | 5 | 10 | 13.3 | 12.42 | 2478081 |
| APP669-711 ($^{15}N$) | 949.84 | 948.34-951.34 | 5 | 10 | 13.3 | 12.42 | 5282503 |
| Aβ40 | 866.84 | 865.34-868.34 | 5 | 10 | 18 | 13.07 | 28242844 |
| Aβ40 ($^{15}N$) | 877.41 | 875.91-878.91 | 5 | 10 | 18 | 13.03 | 45400860 |
| Aβ42 | 903.66 | 902.16-905.16 | 5 | 10 | 18 | 14.15 | 1159165 |
| Aβ42 ($^{15}N$) | 914.63 | 913.13-916.13 | 5 | 10 | 18 | 14.15 | 1288050 |

The last two columns show the retention time at the peak apex, and the total MS intensity value summed up from the isotopomeric peak areas, using one of the plasma IP samples as an example.

Start [min]: MS scan start-time

End [min]: MS scan end-time

CS: charge state

Mass spectrometry data were analyzed using the Skyline software package. The integrated peak areas of precursor [M+1] to [M+5] (for Aβ38, APP669-711 and Aβ40) or precursor [M+2] to [M+4] (for Aβ42) were summed. To get the Aβ42/Aβ40 ratio, endogenous ($^{14}N$) Aβ42 and Aβ40 concentrations from each sample were quantified by normalization to the corresponding internal $^{15}N$ labeled proteins. The final Aβ42/Aβ40 ratio was obtained by dividing the calculated Aβ42 concentration by the calculated Aβ40 concentration. The CVs for most of the Aβ42/Aβ40 ratio were <5%.

All mass spectrometry and quality control analyses were performed prior to sample unblinding. For batch normalization: All 36 individual samples and QC samples were run on two C4 columns. Samples run on the same column were considered the same batch. Two plasma IP samples with relatively low or high Aβ42/Aβ40 ratio were run with both columns for inter-batch normalization. The Aβ42/Aβ40 ratios data produced from the second column were normalized using the following linear regression equation:

Normalized value=1.38*raw value for the batch−0.038

Amyloid PET Imaging

Amyloid PET was used as the reference standard for brain amyloid pathology. Participants were scanned with 11C Pittsburgh-B (PiB) according to a well-established method. Briefly, PET studies were performed on a Siemens Biograph® PET/CT TruePoint 6 scanner (Siemens Medical Systems, Erlangen, Germany). Ninety minutes of PIB-PET data were acquired, quality checked, motion corrected, and processed with a combination of the SPM8 software package, and in-house code using a graphical approach to calculate distribution volume ratios (DVR) with Logan Plots. PiB PET DVR values were used to determine amyloid positivity with a cutoff value of >1.065 DVR. PET DVR values were also converted to Centiloid values (cutoff>10).

Data Analysis and Statistics

Data analyses were performed in a double-blind and independent manner. The plasma-Aβ measurements were performed at Newomics Inc. without clinical information and PET scan values. The scientist performing MS analyses was completely blind to any PET imaging data. All of the PET imaging data were analyzed at UC Berkeley without any information on plasma-Aβ measurements.

Data were analyzed using Excel and Origin software for statistical analysis and graph plotting. Student t tests were performed for continuous variables and a p value<0.05 was considered statistically significant between two groups. Receiver operating characteristic (ROC) analysis was performed to evaluate the ability of plasma Aβ42/Aβ40 to diagnose amyloid PET status. The cutoff value was determined by maximal Youden Index (Sensitivity+Specificity−1). Spearman correlations were used to evaluate the relationship between amyloid PET Centiloid and plasma Aβ42/Aβ40 values.

Example 5: LC-MS of Lipids from CSF Samples

Materials and Methods

Human CSF and plasma samples. Pooled cerebrospinal fluid samples (CSF) were ordered from Innovative Research, Inc and were stored in a −80° C. freezer until analysis. National Institute of Standards and Technology (NIST) Standard Reference Materials (SRMs) 1950 Metabolites in Human Plasma (SRM1950) was ordered from NIST and stored at −80° C. until analysis. The CSF and plasma samples from control and early-stage Alzheimer's disease were obtained from the Knight Alzheimer's Disease Research Center (Knight ADRC) at Washington University in St. Louis. Twenty-three participants included controls (n=11) and participants having early-stage symptomatic AD (n=12) as indicated by the Clinical Dementia Rating (CDR). AD cases included 8 participants with mild cognitive impairment (MCI), also termed very mild AD (CDR 0.5), and 4 participants with mild AD (CDR 1).

Lipid sample preparation. CSF and plasma samples were thawed at room temperature before lipid extraction. The solvents including chloroform, isopropanol, water, and methanol were HPLC-grade and purchased from Sigma-Aldrich (St. Louis, MO). The lipid standards other than free fatty acids were purchased from Avanti Polar Lipid (Alabaster, AL). The isotope-labeled free fatty acid, d5-DHA, d5-EPA, and d11-AA, were purchased from Sigma-Aldrich (St. Louis, MO). The other lipid internal standards are PC 33:1d7, PC 48:2, PE 33:1d7, PE 4ME 16:0 diether, PG 33:1d7, PG 4ME 16:0 diether, PI 33:1d7, LPC 18:1d7, LPC 14:0, LPE 18:1d7, CE 18:1d7, DAG 33:1d7, TAG 48:1d7, SM 36:2d9, SM 30:1, and Cer 17:0. Total lipids were extracted from 5 μL plasma or 50 μL CSF using a modified Bligh & Dyer method. The extracted total lipids were dried under gas nitrogen and reconstituted in acetonitrile:isopropanol:water (65:30:5, v/v/v, 7.5 mM ammonium formate) for plasma or CSF.

Mass spectrometry analysis. ESI-MS/MS mass spectra were acquired on a TSQ Quantiva triple quadrupole mass spectrometer interfaced with an UltiMate 3000 nanoUPLC system (Thermo Fisher Scientific). The 12.5 μL lipid sample was continuously infused into the mass spectrometer at a flow rate of 450 nL/min through a New Objective PicoTip™ emitter (30 μm ID). The infusing solvent consisted of acetonitrile:isopropanol:water (65:30:5, v/v/v) and 7.5 mM ammonium formate, which was the same as the sample solvent. The scan rate was 1000 Da/sec. Collision induced dissociation (CID) gas was set at 0.5 mTorr. No source fragmentation voltage was applied. The electrospray voltage was set at 2.2 kV and ion transfer tube temperature was set at 300° C. During the 30-min direct infusion, the mass spectra of 12 lipid classes, including charged and neutral lipid classes, were consecutively acquired. Different classes of lipids were scanned at different modes. Precursor ion scan (Prec 184) was applied to detect PC, LPC, and SM. Neutral loss scan (NL141) was applied to detect PE and LPE. The PI, PG, CE, and Cer were detected at NL277, NL189, Prec369, and Prec264, respectively. The collision energy applied in each scan mode was 40 V (Prec184), 30 V (NL141), 36 V (NL277), 24 V (NL189), 36 V (Pre369), and 22 V (Prec264), respectively.

DAG and TAG were scanned by the neutral loss of fatty acyl residues, including NL161 (8:0), NL189 (10:0), NL213 (12:2), NL215 (12:1), NL217 (12:0), NL243 (14:1), NL245 (14:0), NL257 (15:1), NL259 (15:0), NL271 (16:1), NL273 (16:0), NL285 (17:1), NL287 (17:0), NL295 (18:3), NL297 (18:2), NL299 (18:1), NL301 (18:0), NL306 (18:1d7), NL313 (19:1), NL315 (19:0), NL317 (20:6), NL319 (20:5), NL321 (20:4), NL323 (323), NL325 (20:2), NL327 (20:1), NL329 (20:0), NL345 (22:6), NL347 (22:5), NL349 (22:4), NL351 (22:3), NL353 (22:2), NL355 (22:1), NL357 (22:0), NL377 (24:4), NL383 (24:1), and NL385 (24:0). These multiple neutral loss scans of fragmentation enabled the quantification of isobaric TAG species. The collision energy for the loss of fatty acyl residues was 32 V. The mass analyzers were adjusted to achieve a resolution of 0.7 atomic mass (am) unit full width at the half height.

Lipid identification and quantitation. Raw MS data was processed using Thermo Xcalibur 3.0 and MSFileReader software (Thermo Fisher Scientific). Each lipid class was scanned at a specific mode and one continuum spectrum was acquired. At Prec184 mode specifically for PC, there were 29 continuum scans. Using the Xcalibur 3.0 software, the 29 continuum scans of Prec184 were averaged, smoothed, and the peak intensities were determined in the centroid mode at each mass-to-charge ratio (m/z). The data list of mass-to-charge ratios and the corresponding peak intensities were copied and pasted into a Microsoft Excel sheet. Besides the Prec184, the 88 continuum scans of NL141 were also averaged, smoothed, and the peak intensities were pasted into a Microsoft Excel sheet. Similar procedures were performed for NL277 (79 continuum scans), NL189 (130 continuum scans), Prec369 (40 continuum scans), Prec264 (196 continuum scans), and neutral loss of each fatty residue (29 continuum scans). Free fatty acids, free DHA, free EPA, and free AA, were detected by selected ion monitoring (SRM) and quantified by the corresponding isotope-labeled internal standard.

A software tool developed in house was used to automatically average and smooth the continuum scans at each scan mode and transfer peak intensities into separate Microsoft Excel sheets. Identification of the peaks of interest and calculation of lipid species amounts were performed using consoles in Microsoft Excel (herein designated as LipidExcel). Corrections for overlap of isotopic variants were applied. The lipids in each class were quantified using the internal standards of that class, respectively. The lipids chosen as the internal standards were not present endogenously in measurable quantities in plasma or CSF samples. Student's t-test was applied to test the difference in lipid species between different groups of samples.

Spearman Correlation Analysis. Spearman correlation between CSF and paired plasma samples was analyzed for the lipid species that were both measured in CSF and plasma. The correlation analyses were performed for species in each of the 12 lipid classes, including PC, LPC, PE, LPE, PI, PG, SM, Cer, DAG, CE, TAG, and FFA. There are 38 SM species that were measured in both CSF and plasma. Spearman correlation value was calculated for each of the SM species, e.g. SM d31:1, in two groups, CDR 0 and CDR 0.5/1. There were 11 participants in the CDR 0 group. For these 11 participants, 11 data points of SM d31:1 in CSF and the paired 11 data points of SM d31:1 in plasma were calculated for correlation value, herein designated as r1 value. The calculated r1 value of SM d31:1 is 0.264, which is positive (+) and indicating a positive correlation between lipid species SM d31:1 of CSF and plasma. There were 12 participants in the CDR 0.5/1 group. For these 12 participants, 12 data points of SM d31:1 in CSF and the paired 12 data points of SM d31:1 in plasma were calculated for correlation value, herein designated as r2 value. The calculated r2 value of SM d31:1 is −0.175, which is negative (−) and indicating a negative correlation relationship between lipid species SM d31:1 of CSF and plasma. Therefore, r1 and r2 are positive and negative for SM d31:1 species (+/−) in CDR 0 and CDR 0.5/1, respectively. Of the 38 SM species, 3 of them are +/+, 9 species are −/−, 25 species are +/−, 1 species are −/+ for CDR 0 and CDR 0.5/1, respectively. Of the 38 SM species, the correlation relationship of 12 SM species maintained same direction in CDR 0 and CDR 0.5/1 (32%, +/+ and −/−), while 26 SM species changed direction in two groups (68%, +/− and −/+).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for determining a likelihood that a subject has Alzheimer's Disease, comprising:

(a) via immunoprecipitation, enriching a biological sample of said subject for proteins that are associated with said Alzheimer's Disease;

(b) directing a liquid medium comprising at least a subset of said proteins enriched in (a) to flow through a microfluidic device to separate individual proteins of said at least said subset of said proteins from one another;

(c) performing a targeted mass spectrometry (MS) on separated individual proteins obtained in (b) by selecting a preferred charge state of a subset of said individual proteins and generating signals assignable to said subset of individual proteins or fragments thereof; and (d) determining, based at least in part on said signals generated in (c), said likelihood that said subject is positive for said Alzheimer's Disease.

2. The method of claim 1, wherein said determining in (d) comprises determining a quantity for each of said subset of individual proteins.

3. The method of claim 1, wherein said determining in (d) further comprises determining a ratio of at least two individual proteins of said subset of individual proteins.

4. The method of claim 1, wherein said proteins comprise amyloid proteins.

5. The method of claim 1, wherein said proteins comprise P-amyloid proteins.

6. The method of claim 4, wherein said proteins comprise Ap38, APP669-711, Ap40, Ap42, or any combination thereof.

7. The method of claim 6, wherein said determining in (d) further comprises determining a ratio of said Ap40 and said Ap42.

8. The method of claim 6, wherein said determining in (d) further comprises determining a ratio of said APP669-711 and said Ap42.

9. The method of claim 1, wherein said individual proteins have not been subjected to an enzymatic digestion process prior to (c).

10. The method of claim 9, wherein said individual proteins are intact proteins.

11. The method of claim 7, further comprising determining said likelihood when said ratio of said Ap40 and said Ap42 is below a pre-determined threshold.

12. The method of claim 11, wherein said pre-determined threshold is between 0 and 0.1770.

13. The method of claim 12, wherein said pre-determined threshold is about 0.1485.

14. The method of claim 1, wherein said biological sample comprises a fluid.

15. The method of claim 1, wherein said biological sample comprises blood or plasma.

16. The method of claim 1, wherein said biological sample comprises a whole blood sample.

17. The method of claim 1, wherein said biological sample has a volume of less than 20 microliter (μL).

18. The method of claim 17, wherein said biological sample has a volume of less than 10 μL.

19. The method of claim 1, wherein (b) comprises directing said liquid medium to flow through said microfluidic device with a flow rate of greater than 10 microliter/minute (μL/min).

20. The method of claim 19, wherein (b) comprises directing said liquid medium to flow through said microfluidic device with a flow rate of greater than 1 μL/min.

* * * * *